(12) United States Patent
Kreuzer et al.

(10) Patent No.: US 11,752,027 B2
(45) Date of Patent: Sep. 12, 2023

(54) DEVICES AND METHODS FOR GUIDING AND APPLYING TRACTION TO A PATIENT'S LEG DURING SURGERY

(71) Applicant: INNOVATIVE ORTHOPEDIC TECHNOLOGIES, IOT AG, Baar (CH)

(72) Inventors: Stefan Kreuzer, Houston, TX (US); Manfred Menzi, Buchs (CH); Kurt Stark, Berg (CH)

(73) Assignee: Innovative Orthopedic Technologies, IOT AG

( * ) Notice: Subject to any disclaimer, the term of this patent is extended or adjusted under 35 U.S.C. 154(b) by 45 days.

(21) Appl. No.: 17/364,452

(22) Filed: Jun. 30, 2021

(65) Prior Publication Data
US 2021/0322198 A1    Oct. 21, 2021

Related U.S. Application Data

(63) Continuation of application No. 15/933,734, filed on Mar. 23, 2018, now Pat. No. 11,051,965, which is a continuation of application No. 14/589,963, filed on Jan. 5, 2015, now Pat. No. 9,949,861.

(60) Provisional application No. 61/923,453, filed on Jan. 3, 2014.

(51) Int. Cl.
 *A61F 5/048* (2006.01)
 *A61H 1/02* (2006.01)

(52) U.S. Cl.
 CPC ............. *A61F 5/048* (2013.01); *A61H 1/02* (2013.01); *A61H 1/0218* (2013.01); *A61H 2201/0173* (2013.01); *A61H 2201/0176* (2013.01); *A61H 2201/0192* (2013.01); *A61H 2201/1253* (2013.01); *A61H 2201/1642* (2013.01); *A61H 2201/1664* (2013.01); *A61H 2201/1671* (2013.01); *A61H 2201/5041* (2013.01); *A61H 2203/0443* (2013.01); *A61H 2205/10* (2013.01)

(58) Field of Classification Search
 CPC ... A61F 5/048; A61F 5/00; A61F 5/37; A61B 17/56; A61B 19/02; A61B 19/08; A61B 17/02; A61B 17/60; A61H 1/02; A61H 2205/10; A61H 2205/106; A61H 2205/108
 See application file for complete search history.

(56) References Cited

U.S. PATENT DOCUMENTS 4,782,827 A * 11/1988 Paratte .................. A61F 5/0127
                                                       5/651
5,645,079 A *  7/1997 Zahiri ................... A61F 5/3769
                                                       5/624

(Continued)

*Primary Examiner* — Ophelia A Hawthorne
(74) *Attorney, Agent, or Firm* — Conley Rose, P.C.

(57) ABSTRACT

A freestanding system for applying traction to a patient independent of a table or bed includes a base including a body and a stabilizer arm moveably coupled to the body, wherein the stabilizer arm has a first end pivotally coupled to the body and a second end distal the body, and wherein the stabilizer arm is configured to pivot about the corresponding first end, and a pad coupled to the second end of the stabilizer arm, wherein the pad includes a suction device configured to releasably secure the second end of the corresponding stabilizer arm to the ground, wherein the pads are configured to maintain the position of the system in response to the application of traction to the patient.

20 Claims, 30 Drawing Sheets

(56) References Cited

U.S. PATENT DOCUMENTS

2007/0161935 A1* 7/2007 Torrie .................... A61G 13/12
602/32
2010/0263129 A1* 10/2010 Aboujaoude ......... A61F 5/3761
5/648

* cited by examiner

US 11,752,027 B2

DEVICES AND METHODS FOR GUIDING AND APPLYING TRACTION TO A PATIENT'S LEG DURING SURGERY

CROSS-REFERENCE TO RELATED APPLICATIONS

This application is a continuation of U.S. non-provisional patent application Ser. No. 15/933,734 filed Mar. 23, 2018, entitled "Devices and Methods for Guiding and Applying Traction to a Patient's Leg During Surgery," which is a continuation of U.S. non-provisional patent application Ser. No. 14/589,963 filed Jan. 5, 2015, entitled "Devices and Methods for Guiding and Applying Traction to a Patient's Leg During Surgery," now U.S. Pat. No. 9,949,861, issued Apr. 24, 2018, which claims benefit of U.S. provisional patent application No. 61/923,453 filed Jan. 3, 2014, all of which are incorporated herein by reference in their entirety.

STATEMENT REGARDING FEDERALLY SPONSORED RESEARCH OR DEVELOPMENT

Not applicable.

BACKGROUND

Embodiments described herein relate generally devices and methods for supporting and manipulating a patient's leg and foot during surgery (e.g., hip joint surgery) or diagnostic procedure. More specifically, embodiments described herein relate to devices and methods for guiding and applying traction to a patient's leg during surgery or diagnostic procedure.

During surgery on a patient's leg (e.g., hip or knee surgery), certain positions and orientations of the leg may be preferred by the surgeon. For example, during one phase of hip surgery, the surgeon may want to place the patient's leg in tension (i.e., traction), whereas in another phase of hip surgery, the surgeon may want to rotate the patient's leg about a certain axis while maintaining traction. Moreover, in some cases, the surgeon may want to maintain traction or a particular rotational orientation of the patient's leg while adjusting the other. For example, during a hip replacement surgery, the patient typically lies on an operating table having a leg holding and support device attached thereto. The leg holding and support exerts tension on the patient's leg while holding the patient's leg in one or more desired positions to facilitate the surgery.

Some conventional leg holding and support devices enable traction to be applied to the patient's leg, but provide limited, if any, ability to simultaneously rotate the patient's leg about one or more axes. Other conventional leg holding and support devices enable rotation of the patient's leg about one or more axes, but do not provide the ability to independently control and adjust the rotation of the patient's leg about different axes. Still other conventional leg holding and support devices enable traction and rotation of the patient's leg about an axis simultaneously, but do not allow adjustment of one while maintaining the other.

BRIEF SUMMARY OF THE DISCLOSURE

An embodiment of a freestanding system for applying traction to a patient independent of a table or bed comprises a base including a body and a stabilizer arm moveably coupled to the body, wherein the stabilizer arm has a first end pivotally coupled to the body and a second end distal the body, and wherein the stabilizer arm is configured to pivot about the corresponding first end, and a pad coupled to the second end of the stabilizer arm, wherein the pad comprises a suction device configured to releasably secure the second end of the corresponding stabilizer arm to the ground, wherein the pads are configured to maintain the position of the system in response to the application of traction to the patient. In some embodiments, the pad has a locked position with the pad fixably secured to the ground and an unlocked position with the pad released from the ground. In some embodiments, the system comprises an actuator configured to transition the pads between the locked positions and the unlocked positions. In certain embodiments, the actuator comprises an air pump configured to selectably generate and relieve a pressure differential between within the suction devices and air in a surrounding ambient environment. In certain embodiments, the air pump is electronically controlled. In some embodiments, the system comprises a boot moveably coupled to the base, wherein the boot is configured to receive and retain at least a portion of a foot of the patient, wherein the pad is configured to resist loads applied to the boot. In certain embodiments, the pad comprises an outer housing coupled to the second end of the corresponding stabilizer arm, a suction cup disposed within the housing, an actuator pivotally coupled to second end of the corresponding stabilizer arm, and a coupling link extending between the actuator and the suction cup, wherein the actuator is configured to transition the corresponding pad between the locked position and the unlocked position. In some embodiments, the system comprises a vertically extendable post having a first end coupled to the base and a second end distal the base, a carrier pivotally coupled to the second end of the post, wherein the carrier is configured to pivot about a horizontal axis relative to the post, a first guide rail coupled to the carrier and configured to pivot with the carrier relative to the post, wherein the first guide rail has a longitudinal axis, a second guide rail pivotally coupled to the first guide rail, wherein the second guide rail is configured to move axially along the first guide rail, and a boot moveably coupled to the second guide rail, wherein the boot is configured to receive and retain at least a portion of a foot of the patient. In some embodiments, the boot is pivotably coupled to the second guide rail and is configured to pivot relative to the second guide rail about a pivot axis disposed in a vertical plane oriented perpendicular to a longitudinal axis of the second elongate guide rail. In certain embodiments, the boot is rotatably coupled to the second guide rail and configured to rotate about a rotational axis oriented perpendicular to a rigid sole of the boot, and the system further comprises a release mechanism coupled to the boot, wherein the release mechanism has a locked position preventing rotation of the boot about the rotational axis and an unlocked position allowing rotation of the boot about the rotational axis. In certain embodiments, the boot is movably coupled to the first elongate guide rail with a carriage, and wherein the carriage is configured to be controllably moved axially relative the first elongate guide rail, and the carriage is configured to move axially relative the first elongate guide rail in a first axial direction and a second axial direction by rotating a spindle gear disposed in the carriage, and wherein the carriage is configured to move axially relative to the first elongate guide rail in the second axial direction in response to the application of a force in the second axial direction to the carriage.

An embodiment of a freestanding system for applying traction to a patient independent of a table or bed comprises a base positionable on the ground and including a body and a stabilizer arm pivotally coupled to the body, wherein the stabilizer arm has a first end pivotally coupled to the body and a second end distal the body, and wherein the stabilizer arms are configured to pivot about the first ends, and a pad coupled to the second end of the stabilizer arm, wherein the pad comprises an actuator configured to selectively apply a low pressure region between the pad and the ground to releasably secure the second end of the corresponding stabilizer arm to the ground. In some embodiments, the actuator comprises an air pump. In some embodiments, the air pump is electronically controlled. In certain embodiments, the pad comprises an outer housing coupled to the second end of the corresponding stabilizer arm, a suction cup disposed within the housing, a coupling link extending between the actuator and the suction cup, and wherein the actuator is coupled to the second end of the corresponding stabilizer. In certain embodiments, the actuator comprises a handle actuatable between an unlocked position and a locked position configured to form the vacuum between the pad and the ground. In some embodiments, the pad comprises a suction device configured to resist loads applied to the system. In some embodiments, the system comprises a vertically extendable post having a first end coupled to the base and a second end distal the base, a carrier pivotally coupled to the second end of the post, wherein the carrier is configured to pivot about a horizontal axis relative to the post, a first guide rail coupled to the carrier and configured to pivot with the carrier relative to the post, wherein the first guide rail has a longitudinal axis, a second guide rail pivotally coupled to the first guide rail, wherein the second guide rail is configured to move axially along the first guide rail, and a boot moveably coupled to the second guide rail, wherein the boot is configured to receive and retain at least a portion of a foot of the patient. In some embodiments, the boot is pivotably coupled to the second guide rail and is configured to pivot relative to the second guide rail about a pivot axis disposed in a vertical plane oriented perpendicular to a longitudinal axis of the second elongate guide rail, wherein the boot is rotatably coupled to the second guide rail and configured to rotate about a rotational axis oriented perpendicular to a rigid sole of the boot. In some embodiments, the system comprises a release mechanism coupled to the boot, wherein the release mechanism has a locked position preventing rotation of the boot about the rotational axis and an unlocked position allowing rotation of the boot about the rotational axis.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
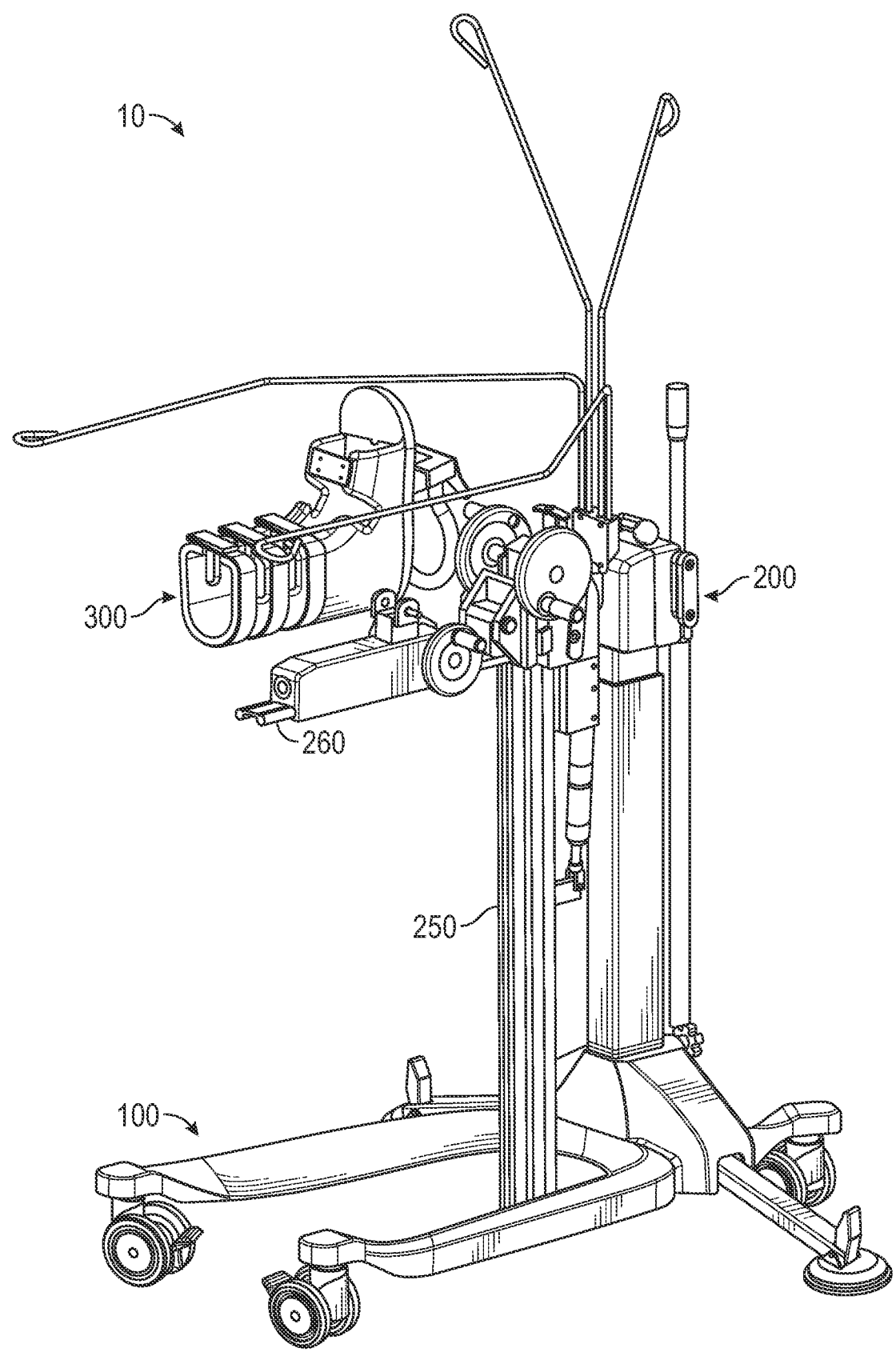
FIG. 1 is a perspective view of an embodiment of a leg support and manipulation system in accordance with the principles disclosed herein.
Figure 2:
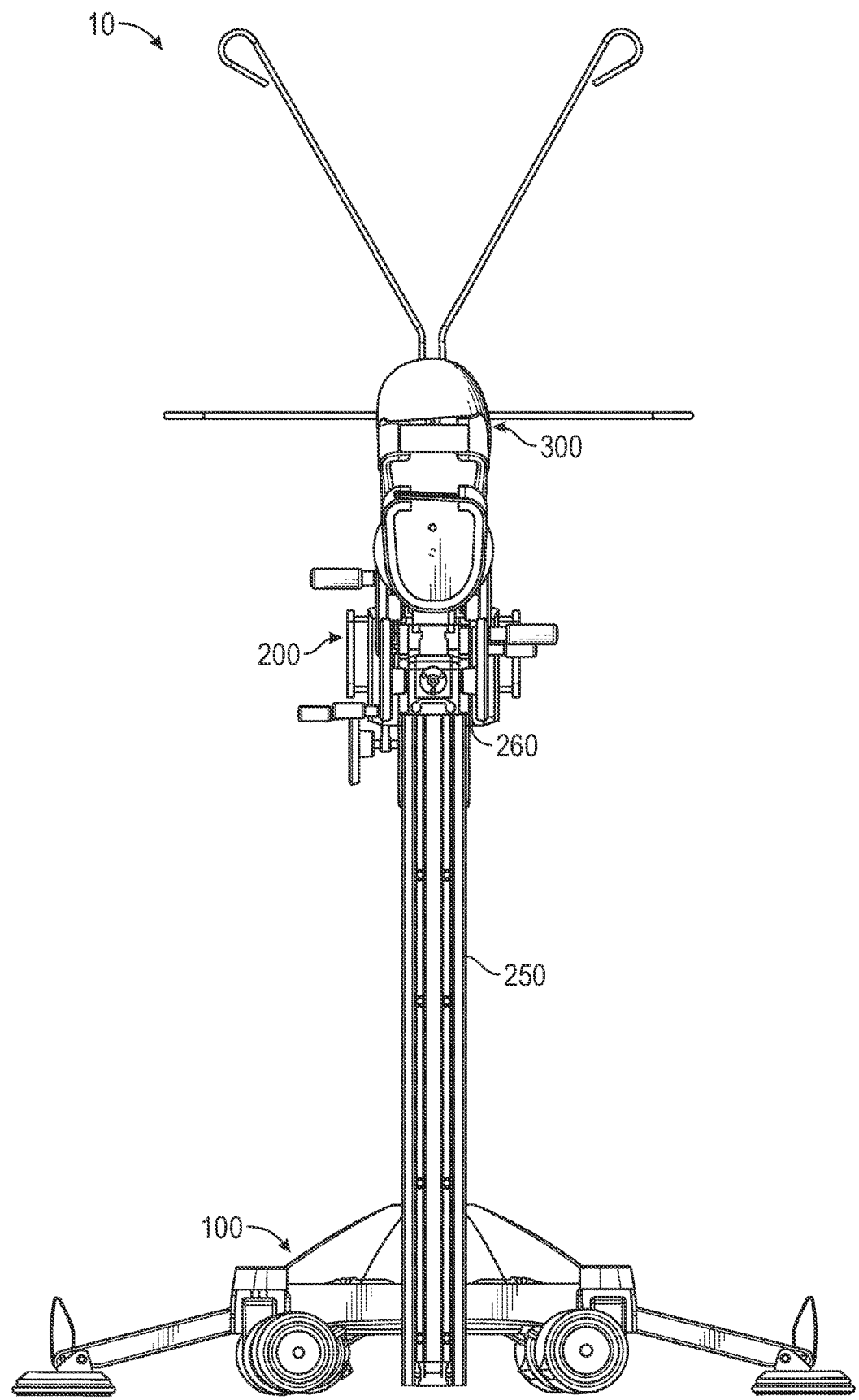
FIG. 2 is a front view of the system of FIG. 1.
Figure 3:
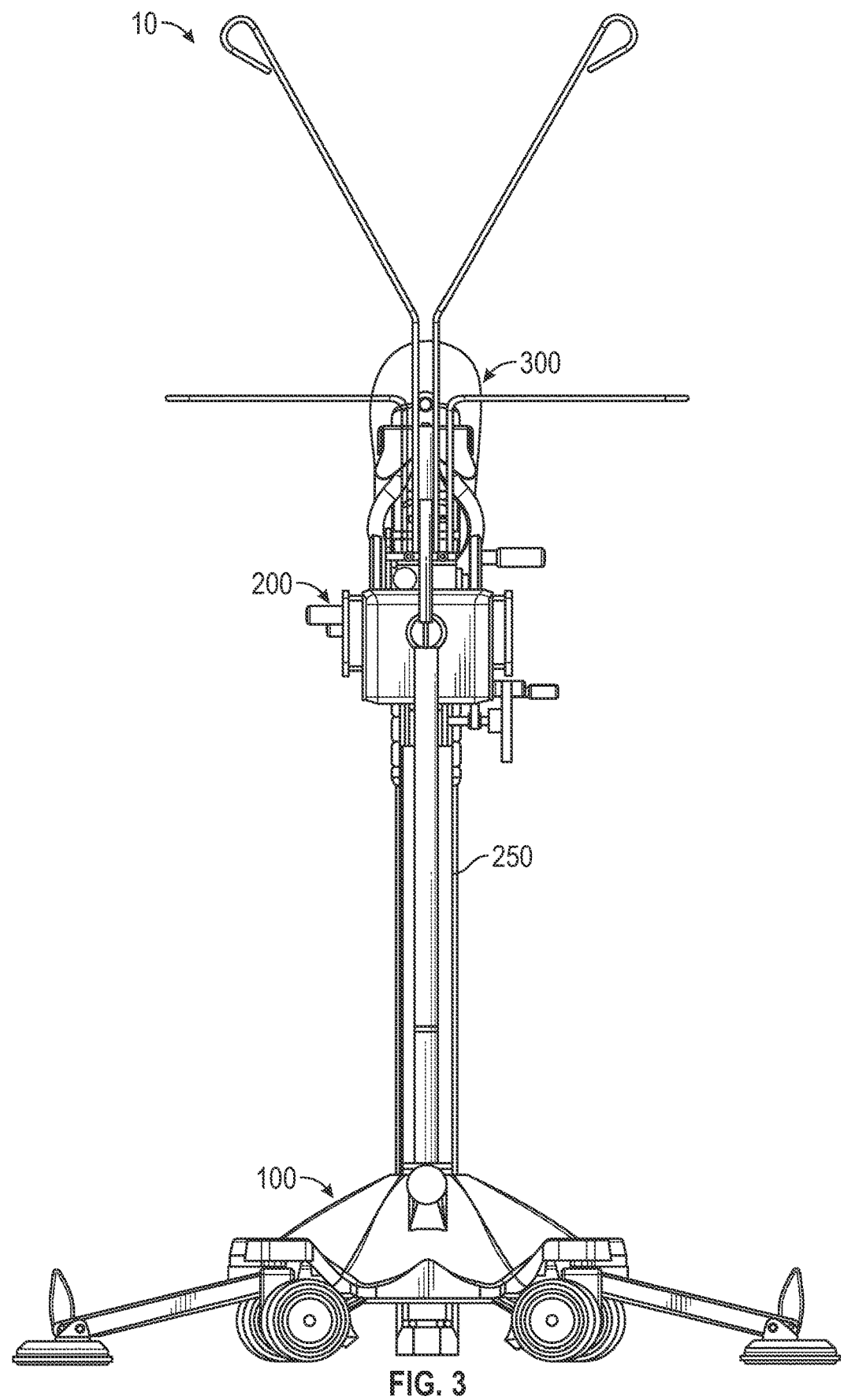
FIG. 3 is a rear view of the system of FIG. 1.
Figure 4:
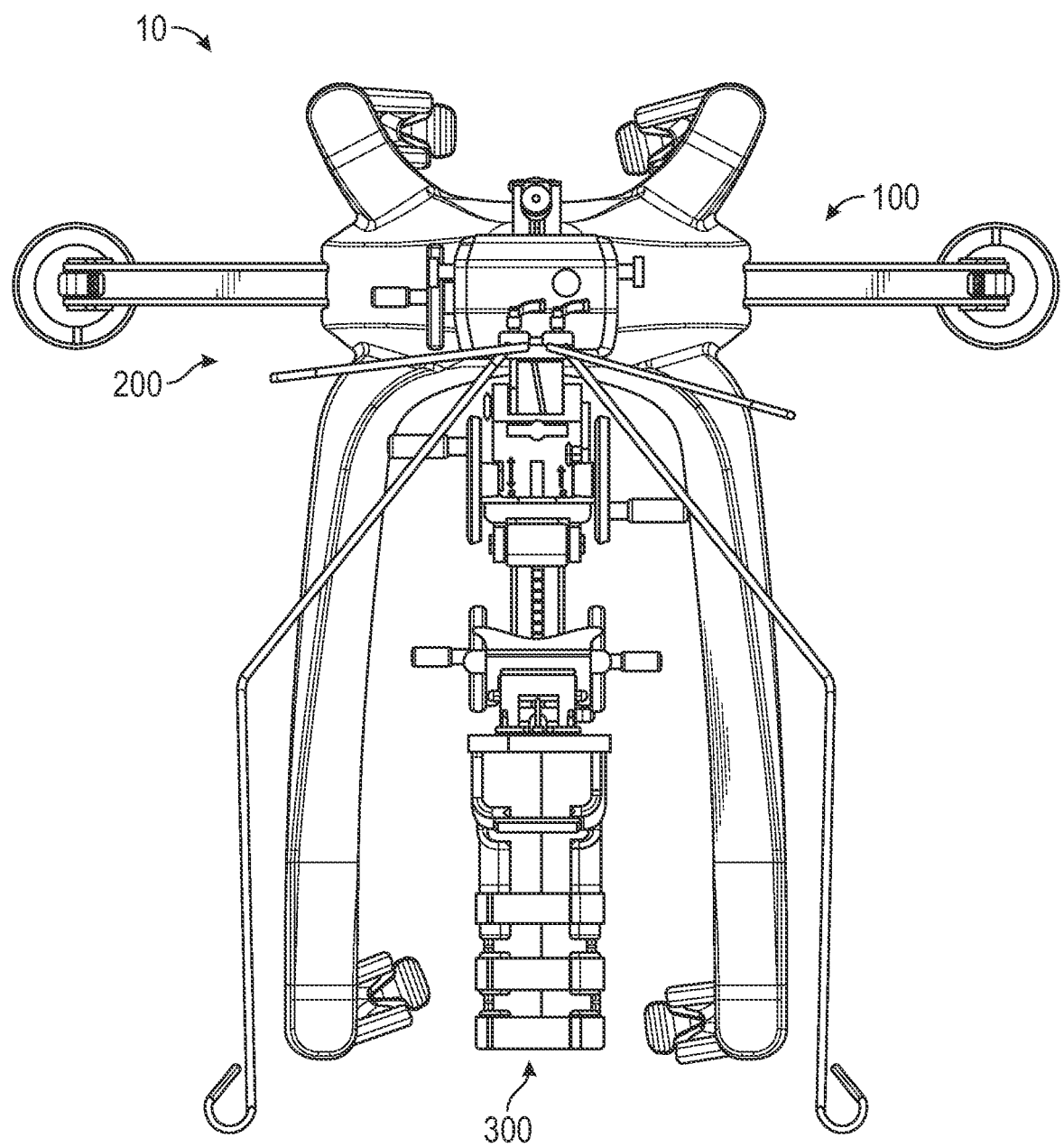
FIG. 4 is a top view of the system of FIG. 1.
Figure 5:
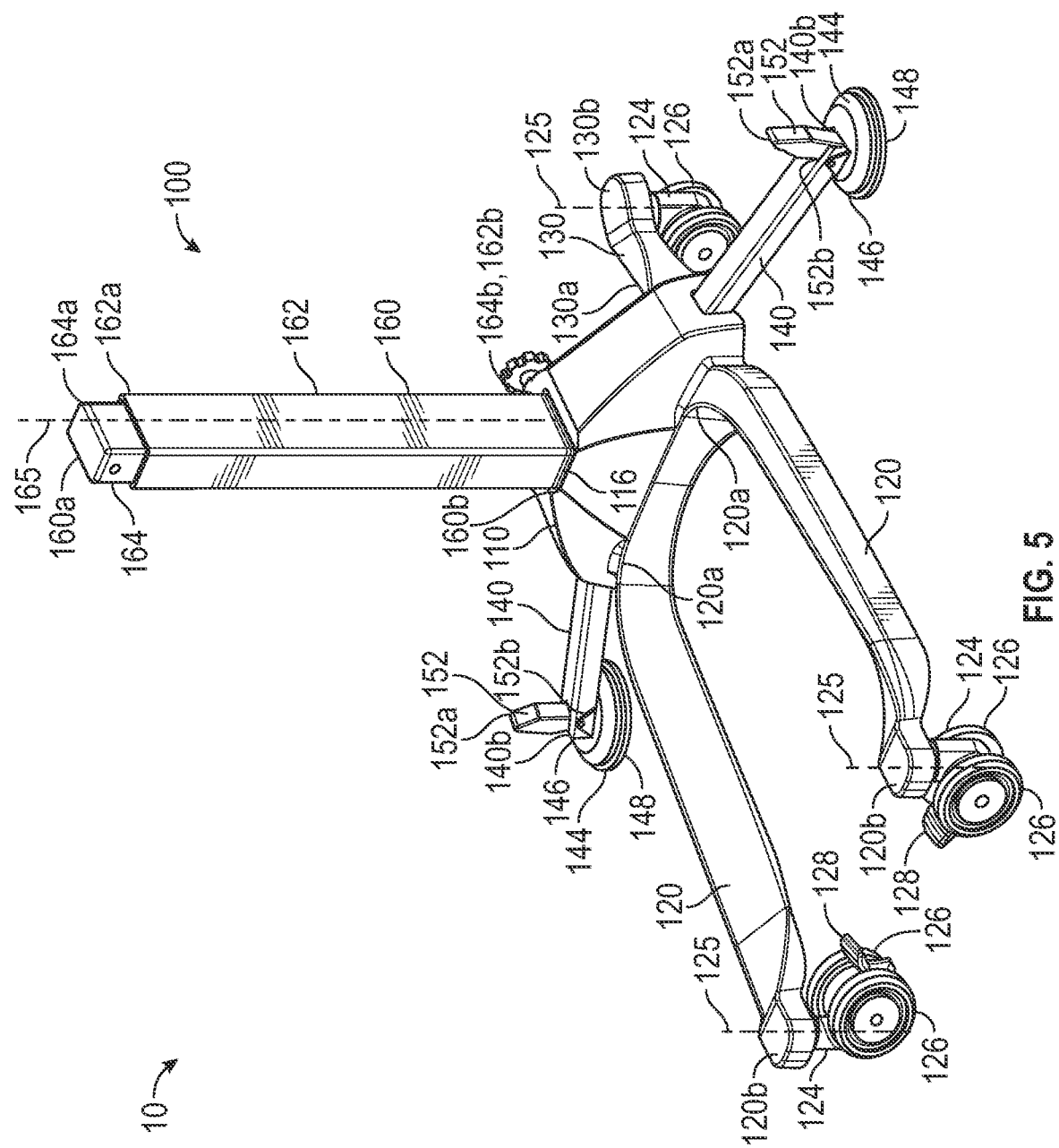
FIG. 5 is a front perspective view of the support assembly of the system of FIG. 1.
Figure 6:
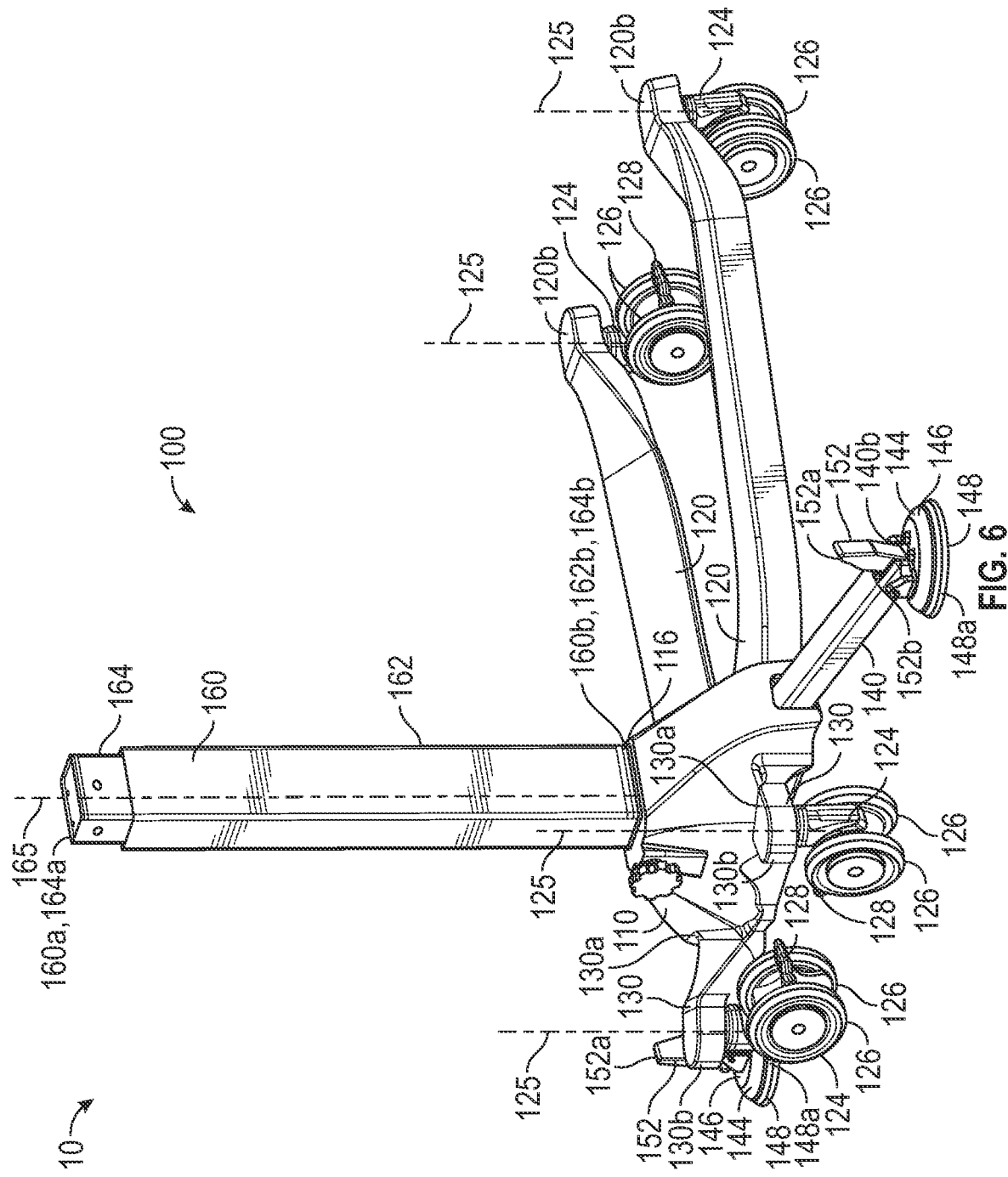
FIG. 6 is a rear perspective view of the support assembly of FIG. 5.
Figure 7:
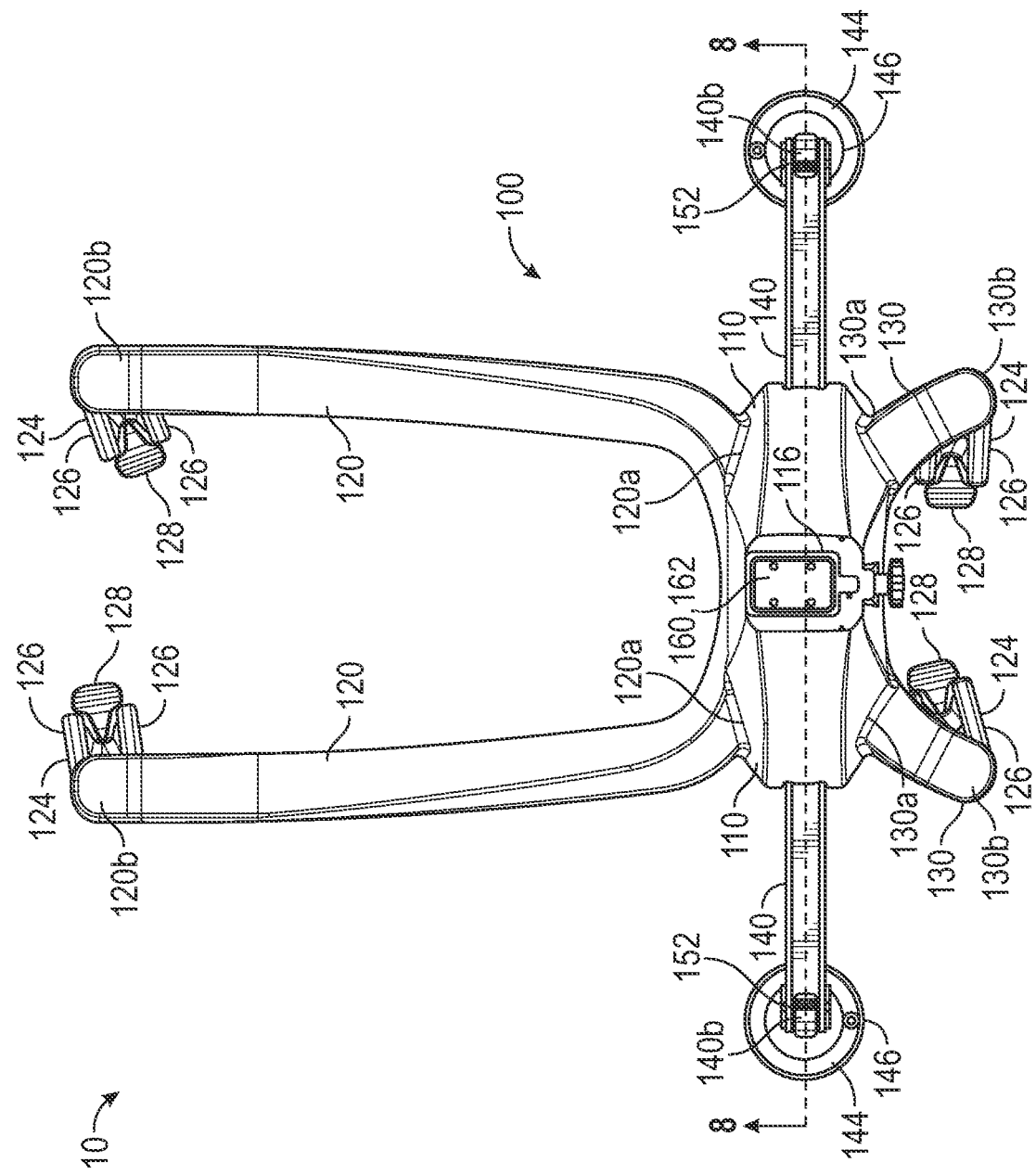
FIG. 7 is a top view of the support assembly of FIG. 5.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. Further, as used herein, the terms "bed" and "table" refer to a patient's bed, operating table, examination bed, or any other bed used for medical procedures, operations, care, diagnostics, or combinations thereof.

Referring now to FIGS. 1-4, an embodiment of a leg support and manipulation system 10 is shown. System 10 is configured to selectively and controllably secure, hold, support, manipulate, position, and orient a patient's leg during a surgical or diagnostic procedure. During such a procedure, the patient is positioned on a bed or operating table, and the system 10 is positioned adjacent the end of the table to hold and support one of the patient's legs. Thus, contrary to many conventional leg support and manipulation devices, system 10 is "freestanding." In other words, during a patient procedure, system 10 is separate and spaced apart from the table. In general, system 10 can be used to support and manipulate the patient's leg undergoing the procedure, referred to herein as the "affected" leg, or the patient's opposite leg (i.e., the patient's leg that is not the subject of the procedure), referred to herein as the "unaffected" leg. As will be described in more detail below, in this embodiment, system 10 facilitates a sterile operating environment with the use of a sterile drape, and further, system 10 is modular such that individual assemblies and components of system 10 may be selectively and independently sterilized.

Leg support and manipulation system 10 is generally configured to stand alone and independently support the patient's affected leg. Specifically, system 10 is configured to support the patient's affected leg without being coupled or in physical engagement with an operating table, the patient's bed, or any other device. Thus, system 10 is configured to support the patient's affected leg independently of the operating table and/or the patient's bed.

Referring still to FIGS. 1-4, in this embodiment, leg support and manipulation system 10 includes a support assembly 100 moveably disposed on the ground, a rail assembly 200 coupled to the support assembly 100, and a foot holder assembly 300 coupled to the rail assembly 200. During a procedure, the patient's foot is secured to foot holder assembly 300, which is moveably coupled to a rail assembly 200 and supported by the support assembly 100. Support assembly 100, rail assembly 200, foot holder assembly 300, or combinations thereof can then be employed to position and manipulate the patient's foot and ankle to adjust and achieve the desired position and orientation of the patient's corresponding leg (affected or unaffected leg), as well as controllably apply traction to the patient's corresponding leg.

Referring now to FIGS. 5-8, support assembly 100 allows system 10 to be moved and positioned at the desired location along the ground (e.g., floor of operating room), and then releasably locked and secured at that desired location. Consequently, support assembly 100 transfers the load applied by the rail assembly 200, foot holder assembly 300, and the patient's leg to the ground. In this embodiment, support assembly 100 includes a base 110, a first or forward pair of arms 120 extending horizontally from base 110, a second or rearward pair of arms 130 extending horizontally from base 110, a pair of stabilizers 140 pivotally coupled to base 110, and a post assembly 160 extending vertically upward from base 110. Arms 120 extend in the same direction from base 110 and are laterally spaced apart; arms 130 extend in the opposite direction from base 110 as arms 120 and are laterally spaced apart.

Each forward arm 120 has a first or fixed end 120a fixably secured to base 110 and a second or free end 120b distal base 110. A wheel or caster 124 is pivotally coupled to the free end 120b of each forward arm 120 with a vertical shaft (not shown) seated in a mating receptacle in the bottom of the end 120b, which allows the caster 124 to freely rotate relative to the corresponding end 120b about a vertical axis 125. Each caster 124 includes a pair of wheels 126 and a lock 128 configured to releasably lock wheels 126. Each pair of wheels 126 are configured to roll along the ground about a horizontal axis. Each lock 128 has a locked position preventing wheels 126 from rolling along the ground (i.e., preventing wheels 126 from rotating about the horizontal axis) and an unlocked position allowing wheels 126 to roll along the ground (i.e., allow wheels 126 to rotate about the horizontal axis).

In this embodiment, each lock 128 is manually transitioned between the locked and unlocked positions via a foot pedal that can be depressed and raised by the foot of one or more operating room personnel. However, in other embodiments each lock 128 may be mechanically actuated through other mechanisms (e.g., a lock rotated into a locked position by hand). In still other embodiments, each lock 128 may be actuated electrically, hydraulically, or through other means known in the art using an actuator. In general, locks 128 can comprise any wheel locking mechanism known in the art Although locks 128 function to releasably lock wheels 126 to prevent rotation about the horizontal axes in this embodiment, in other embodiments, the locks (e.g., locks 128) simultaneously lock the wheels to prevent rotation about both the horizontal axis and the vertical axis (e.g., axis 125).

Referring still to FIGS. 5-8, rear arms 130 have a first or fixed end 130a fixably secured to base 110 and a second or free end 130b distal base 110. A caster 124 is pivotally coupled to free end 130b of each arm 130. Casters 124 coupled to arms 130 are the same as casters 124 previously described.

Arms 120 have a horizontal length measured between ends 120a, 120b, and arms 130 have a horizontal length measured between ends 130a, 130b. In this embodiment, the horizontal length of each arm 120 is the same, and the horizontal length of each arm 130 is the same. In addition, the horizontal length of each arm 120 is greater than the horizontal length of each arm 130.

Figure 8:
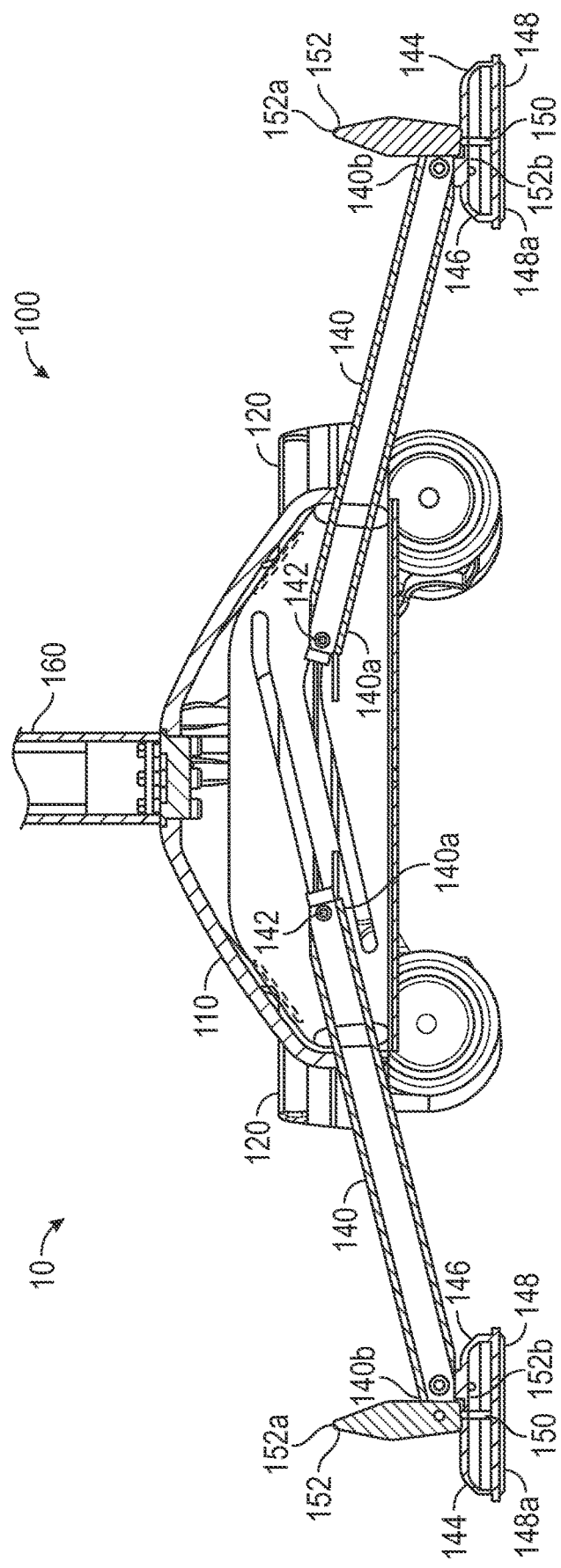
FIG. 8 is a cross-sectional view of the support assembly of FIG. 5 taken along section 8-8 in FIG. 7.
Figure 9:
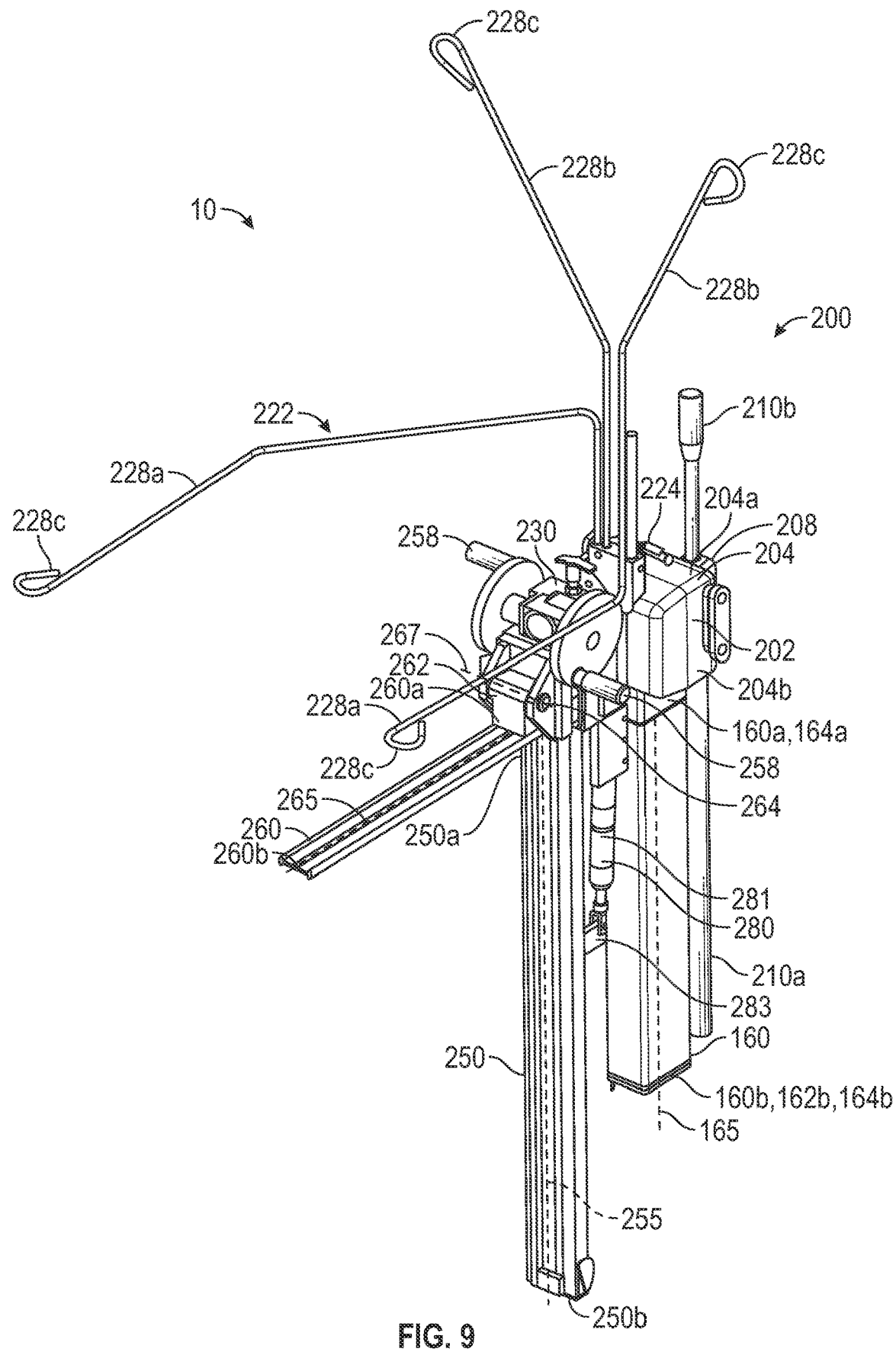
FIG. 9 is a perspective view of a rail assembly of the system of FIG. 1.

Referring still to FIGS. 5-8, stabilizers 140 are disposed between forward arms 120 and rearward arms 130 and extend laterally from opposing sides of base 110. Stabilizers 140 provide added stability to system 10 and releasably secure system 10 to the ground so that it is prevented from moving once disposed at the desired position during use. In this embodiment, each stabilizer includes a first end 140a moveably coupled to base 110 and a second or free end 140b distal base 110. As best shown in FIG. 8, the first end 140a of each stabilizer 140 is coupled to base 110 at a pivot point 142, which allows the stabilizer 140 to rotate up and down about a horizontal axis extending through pivot point 142. Thus, each stabilizer 140 can pivot about its end 140a between a retracted or raised position with distal end 140*b* spaced above the ground and a deployed or lowered position with distal end 140*b* firmly seated against the ground. Each stabilizer 140 can be releasably locked in the raised or deployed position for example by a locking pin or lever.

A pad 144 is disposed at free end 140*b* of each stabilizer 140. Thus, when stabilizers 140 are deployed, pads 144 are seated against the ground to provide lateral support and stability to system 10. More particularly, pads 144 are configured to stabilize system 10 against reaction forces produced by the patient's affected leg during use of system 10 (e.g., when traction is applied to the affected leg with system 10). In this embodiment, pads 144 are suction devices that are releasably secured to the ground via formation of a low pressure region relative to the surrounding ambient pressure. In particular, each pad 144 includes an outer housing 146, a suction cup 148 disposed within housing 146, an actuator 152 pivotally coupled to end 140*b*, and a coupling link 150 extending between actuator 152 and cup 148. The bottom of each housing 146 is open to allow the corresponding suction cup 148 to access and engage the ground therebelow. Each actuator 152 is a foot or hand operated lever having a first end 152*a* distal the corresponding housing 146 and a second end 152*b* engaging the upper surface of the corresponding housing 146. Each actuator 152 is pivotally coupled to end 140*b* of the corresponding stabilizer 140 proximal second end 152*b*. Second end 152*b* of each actuator 152 comprises a cam surface that slidingly engages the top of the corresponding housing 146. Each pad 144 and actuator 152 can be described as having a "locked" position with end 152*a* rotated downward and pad 144 firmly secured to the ground (FIG. 8) and an "unlocked" position with end 152*a* rotated upward and pad 144 released from the ground (i.e., not firmly secured to the ground). With stabilizers 140 in the deployed positions, pads 144 and actuators 152 are transitioned between the locked and unlocked positions by rotating ends 152*a* downward and upward respectively.

In particular, with each stabilizer 140 deployed and the corresponding actuator 152 in the unlocked position, the flexible suction cups 148 are pressed flat or substantially flat against the ground. The annular radially outer edge or lip 148*a* of each suction cup 148 is held in place by the annular rim at the lower end of the corresponding housing 146. When each actuator 152 is transitioned to the locked position by pivoting the corresponding end 152*a* downward towards the ground (e.g., by pushing down on end 152*a*), the corresponding link 150 is pulled upward, thereby pulling the radially inner portions of the corresponding suction cup 148 upward away from the ground. With the lip 148*a* of each cup 148 held against the ground with housing 146, as the radially inner portion of each cup 148 is raised upward, a vacuum or low pressure region (relative to the outside ambient environment) is formed therein (i.e., between the ground and the suction cup 148). Such a vacuum or low pressure region within the cup 148 restricts and/or prevents the corresponding cup 148 and pad 144 from moving relative to the ground, thereby securing that pad 144 and system 10 to the ground. To unlock each pad 144, the corresponding actuator 152 is pivoted about end 152*b* by urging end 152*a* upward away the ground (e.g., by pushing up on end 152*a*), thereby pushing the corresponding link 150 downward toward the ground and pushing the radially inner portion of the corresponding cup 148 downward flat or substantially flat against the ground. As suction cup 148 is pushed to the ground, the low pressure regions within the cup 148 is relieved, thereby equalizing the pressure within suction cup 148 and the surrounding ambient environment and allowing the corresponding pad 144 to be moved relative to the ground.

In this embodiment, each actuator 152 is a manually operated lever that is transitioned between the locked and unlocked positions by depressing end 152*a* or raising end 152*a* with the user's foot. However, in other embodiments, the stabilizer pads (e.g., pads 144) are transitioned between the locked and unlocked positions by other means such as via a personal interface, a switch, computer, or other device operable for applying a vacuum to the pads 140. In such embodiments, an electronically controlled air pump can be employed to generate and relieve the pressure differential.

Post assembly 160 extends vertically upward from base 110 and has a vertically oriented central or longitudinal axis 165, a first or upper end 160*a* distal base 110, and a second or lower end 160*b* releasably secured to base 110 with a coupling 116. In addition, post assembly 160 includes a tubular outer post 162 and an inner post 164 slidingly received in outer post 162. Outer post 162 has a first or upper end 162*a* and a second or lower end 162*b* defining end 160*b* of post assembly 160. Inner post 164 is coaxially disposed within outer post 162 and has a first or upper end 164*a* extending from upper end 162*a* of outer post 162 and a second or lower end 164*b* disposed within outer post 162. Upper end 164*a* defines upper end 160*a* of post assembly 160. In this embodiment, inner post 164 can be controllably moved axially up and down relative to outer post 162 and base 110, thereby vertically and axially extending and contracting post assembly 160. In other words, the axial length of post assembly 160 and the axial position of end 160*a*, 164*a* relative to base 110 can be varied and adjusted as desired by telescopically extending or retracting inner post 164 relative to outer post 162. Once the desired axial position of upper end 160*a* relative to lower end 160*b* is achieved, the axial position of inner post 164 relative to outer post 162, and hence the axial position upper end 160*a*, 164*a* can be releasably locked. As best shown in FIGS. 10, 11, 13, and 14, in this embodiment, post assembly 160 is vertically extended and retracted with an actuator 163 comprising a manually operated hand crank that can be rotated in one direction to extend post assembly 160 (i.e., move inner post 164 upward relative to outer post 162) and rotated in the opposite direction to contract post assembly 160 (i.e., move inner post 164 downward relative to outer post 162). In particular, in this embodiment, inner post 164 is displaced axially (up and down) via a threaded shaft disposed therein and coupled to actuator 163. Rotation of actuator 163 causes the threaded shaft to rotate. The shaft threadably engages a mating block fixably coupled to outer post 162. Thus, rotation of the shaft relative to the block causes inner post 164 to move vertically relative to outer post 162. The mating internal threads of the block and external threads of the shaft are self-locking such that they do not slide or move relative to each other unless actuator 163 is rotated. In this embodiment, post assembly 160 is a spindle lifting column similar to the lifting columns produced by LINAK U.S. Inc., 2200 Stanley Gault Parkway, Louisville, Ky. 40223. Although post assembly 160 is a spindle lifting column extended and contracted by manually rotating an actuator 163 in this embodiment, in general, post assembly 160 can be extended and retracted by any suitable means known in the art including, without limitation, a gear and toothed rack, a linear actuator (e.g., pneumatic or hydraulic piston cylinder assembly), etc.

Referring now to FIGS. 1 and 9-12, rail assembly 200 is coupled to upper end 160*a* of post assembly 160 (upper end 164*a* of inner post 164) and supports, positions, and orients foot holder assembly 300 relative to support assembly 100. For purposes of clarity, foot holder assembly 300 is not shown in FIGS. 9-12. In this embodiment, rail assembly 200 includes a hub or base 202 coupled to upper end 160a of post assembly 160, a carrier 230 pivotally coupled to base 202, a first elongate guide rail 250 fixably coupled to carrier 230, and a second elongate guide rail 260 moveably coupled to first guide rail 250. As will be described in more detail below, foot holder assembly 300 can be controllably moved and locked along second guide rail 260, second guide rail 260 can be controllably moved and locked along first guide rail 250, and carrier 230 can be controllably pivoted and locked relative to base 202 to adjust the angular orientation of guide rails 250, 260 relative to base 202. Although guide rails 250, 260 can pivot relative to base 202 from vertical and horizontal orientations, respectively, first guide rail 250 is generally vertically oriented and second guide rail 260 is generally horizontally oriented. Accordingly, first guide rail 250 may also be referred to as "vertical" guide rail 250 and second guide rail 260 may also be referred to as "horizontal" guide rail 260.

Referring still to FIGS. 9-12, in this embodiment, base 202 includes a rigid outer housing 204, a rotatable horizontal shaft 208 extending through housing 204, and a locking apparatus 214 disposed within housing 204 and coupled to shaft 208. Housing 204 has a first or upper end 204a distal upper end 164a of post 164 and a second or lower end 204b fixably mounted to upper end 164a of the inner post 164. Thus, housing 204 does not move translationally or rotationally relative to inner post 164. As will be described in more detail below, a drape hanger assembly 222 is removably coupled to upper end 204a of housing 204.

Figure 10:
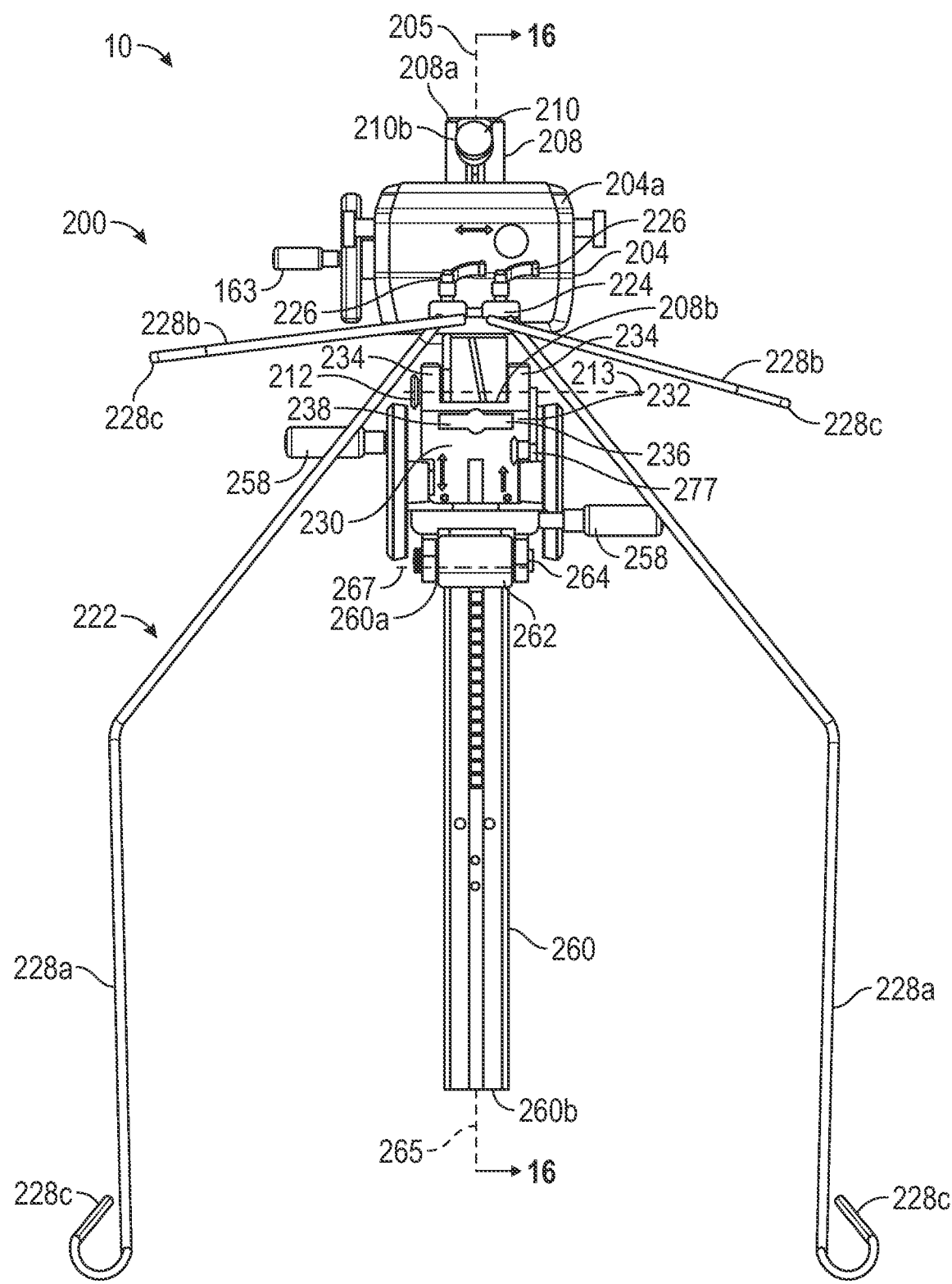
FIG. 10 is a top view of the rail assembly of FIG. 9.
Figure 14:
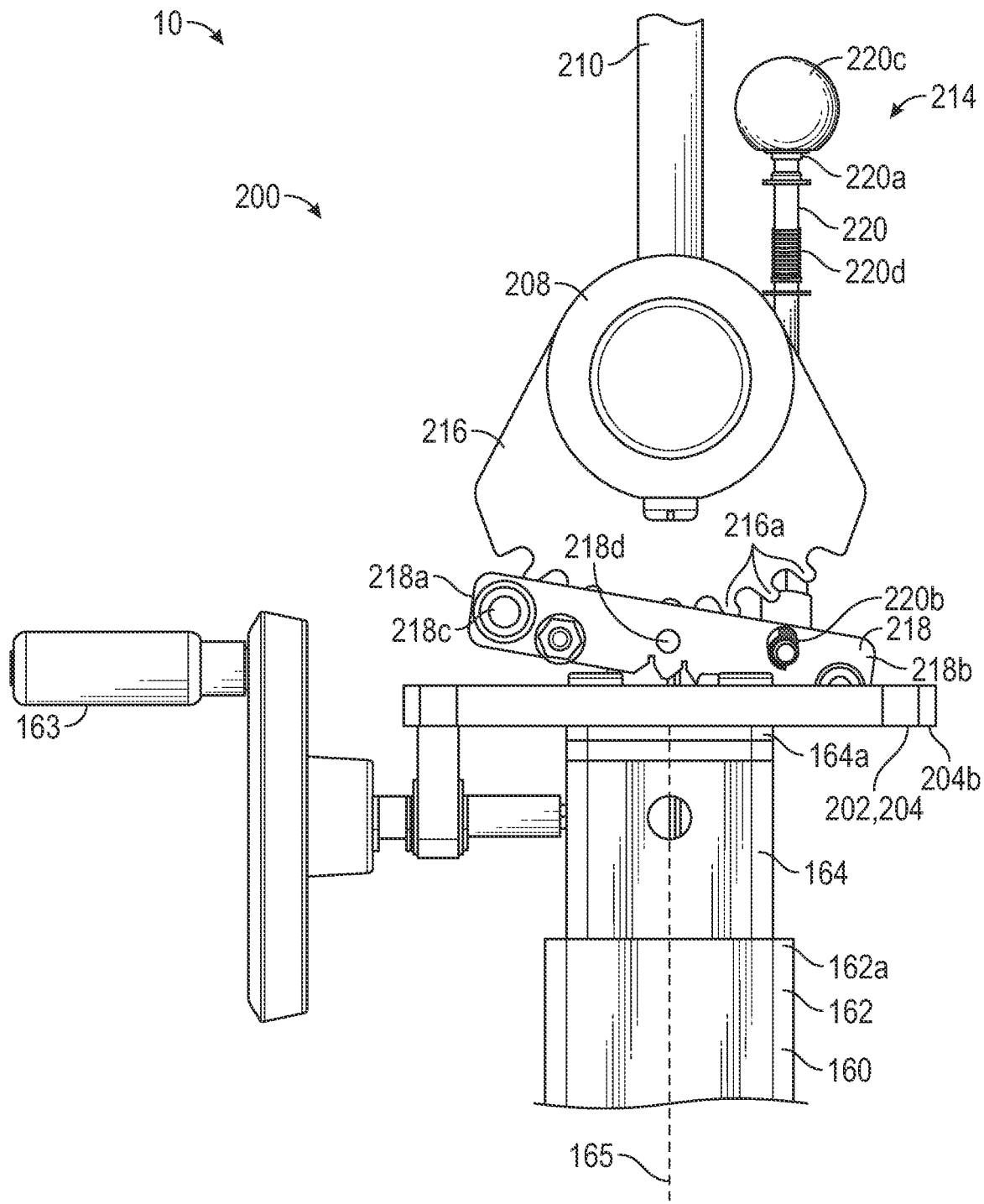
FIG. 14 is a front view of the locking apparatus of FIG. 13.
Figure 15:
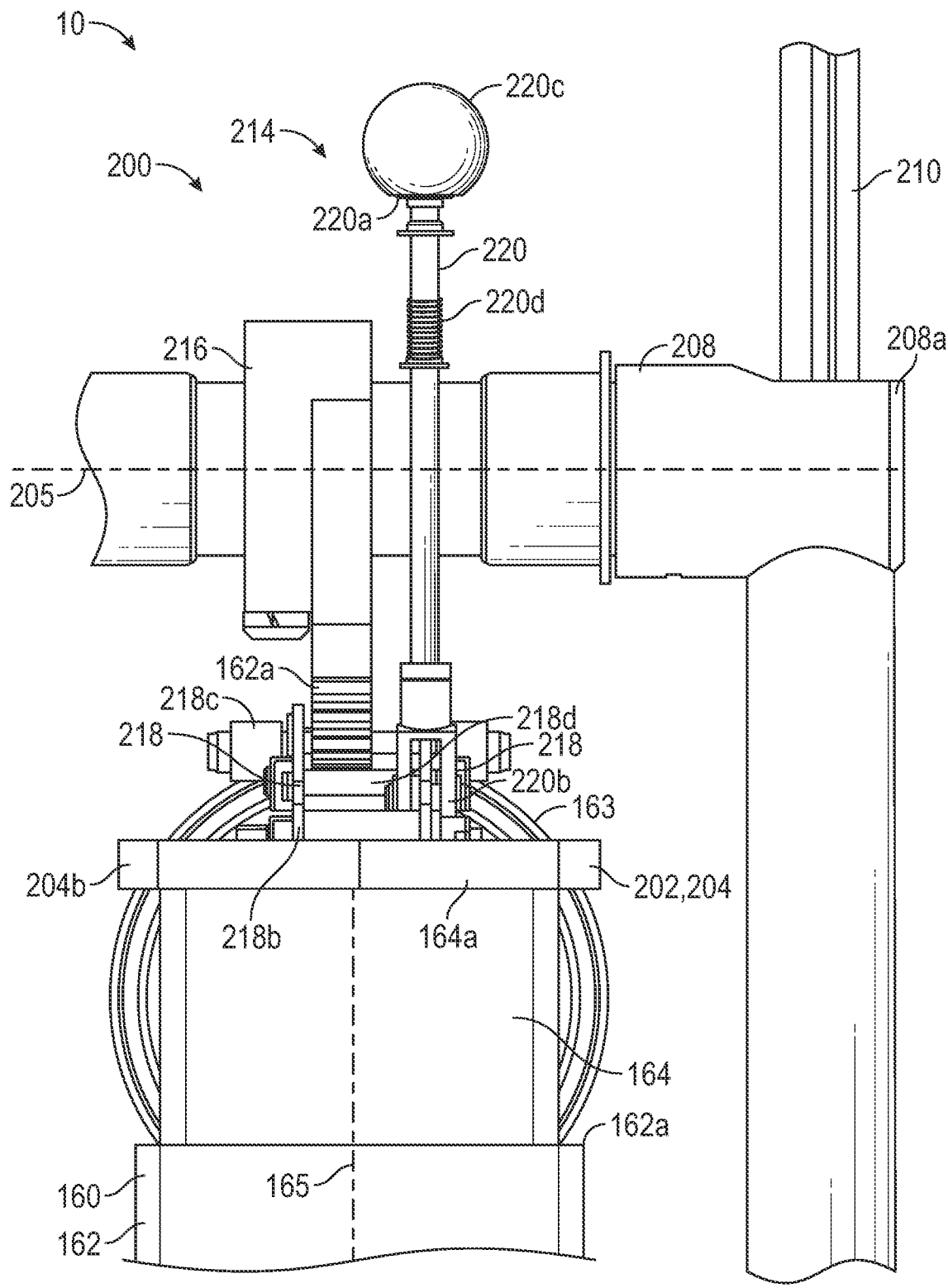
FIG. 15 is a side view of the locking apparatus of FIG. 13.
Figure 16:
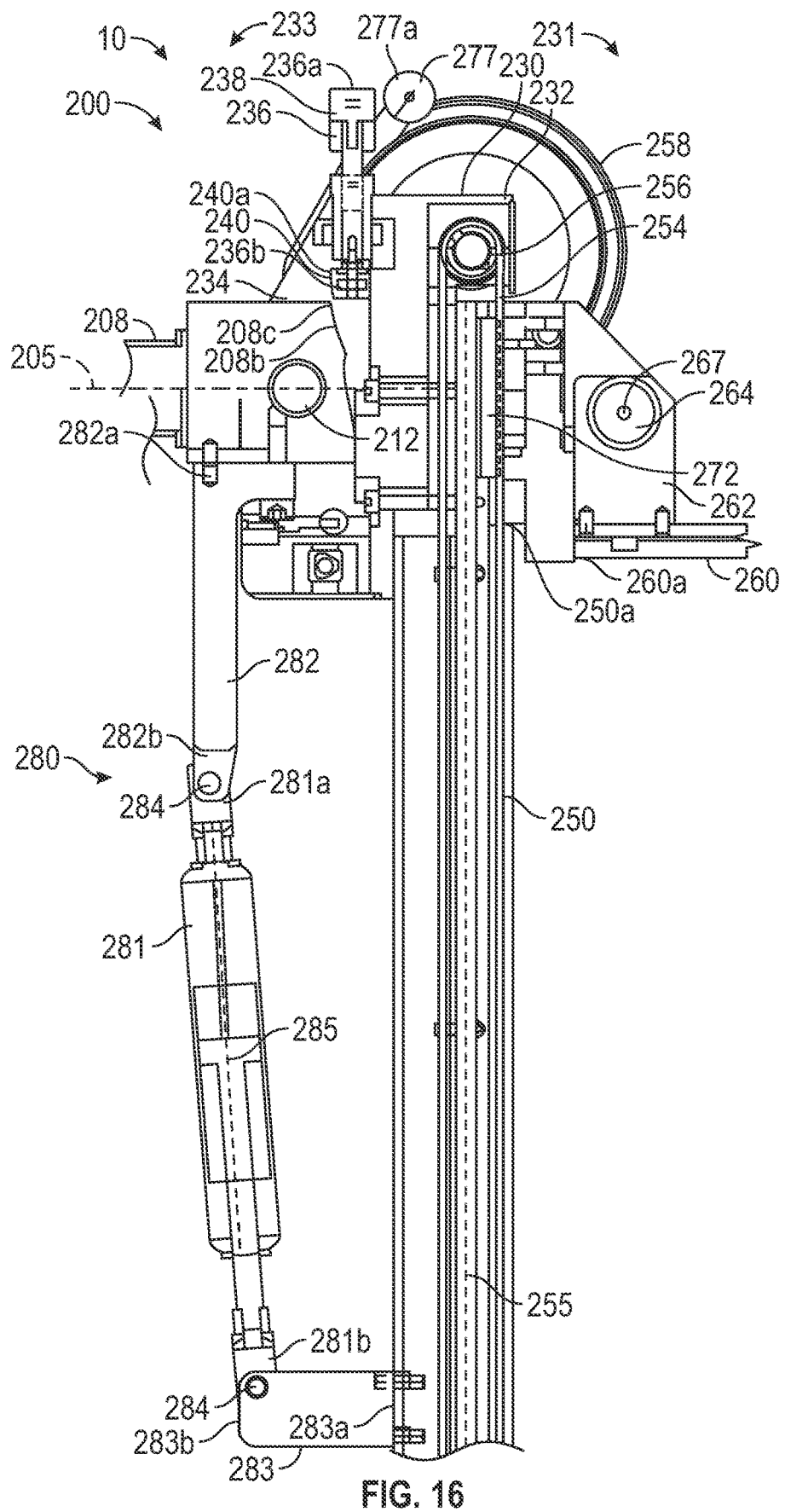
FIG. 16 is a cross-sectional view of the rail assembly of FIG. 9 taken along section 16-16 of FIG. 10.

Referring now to FIGS. 9-16, housing 204 (except for lower end 204b) is hidden for clarity to better illustrate shaft 208 and locking apparatus 214. Shaft 208 has a horizontally oriented central axis 205, a first or outer end 208a coupled to an actuation or operating handle 210, and a second or inner end 208b coupled to carrier 230. As best shown in FIGS. 10 and 16, second end 208b of shaft 208 is pivotally coupled to carrier 230 with a pin 212. In particular, carrier 230 comprises a block 232 and a pair of arms 234 extending from block 232. Arms 234 are disposed on opposite sides of end 208b of shaft 208 and have aligned bores that receive the ends of pin 212. Pin 212 has a central axis 213 that intersects and is oriented perpendicular to axis 205. Pin 212 allows shaft 208 to transfer rotational torque to carrier 230 about axis 205 while simultaneously allowing carrier 230 to pivot about axis 213 relative to base 202. Thus, handle 210 can be rotated within a vertical plane to apply rotational torque to carrier 230 via shaft 208 and pin 212, thereby enabling an operator of system 10 to controllably rotate shaft 208 and carrier 230 in either direction about horizontal axis 205.

Figure 11:
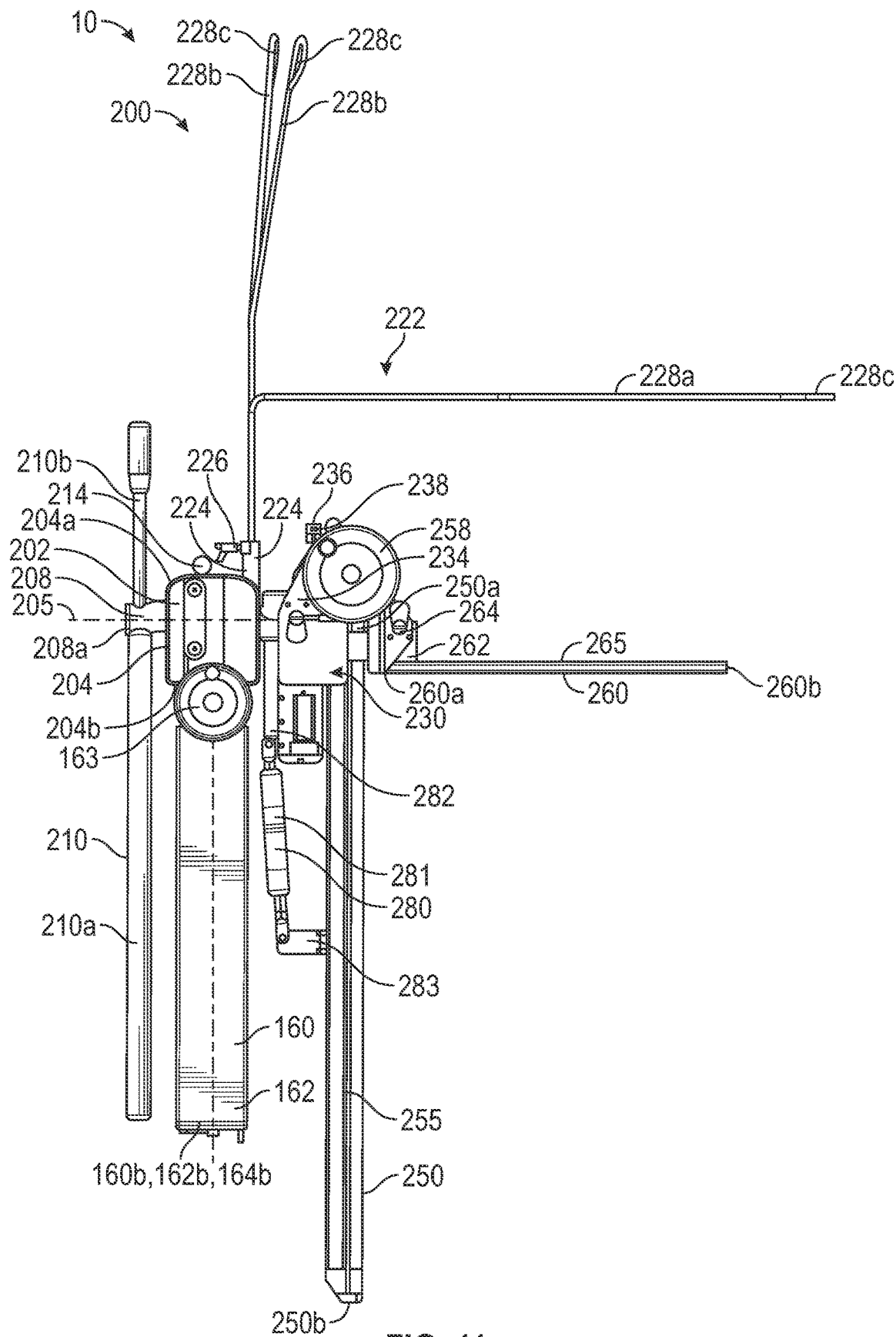
FIG. 11 is a side view of the rail assembly of FIG. 9.
Figure 12:
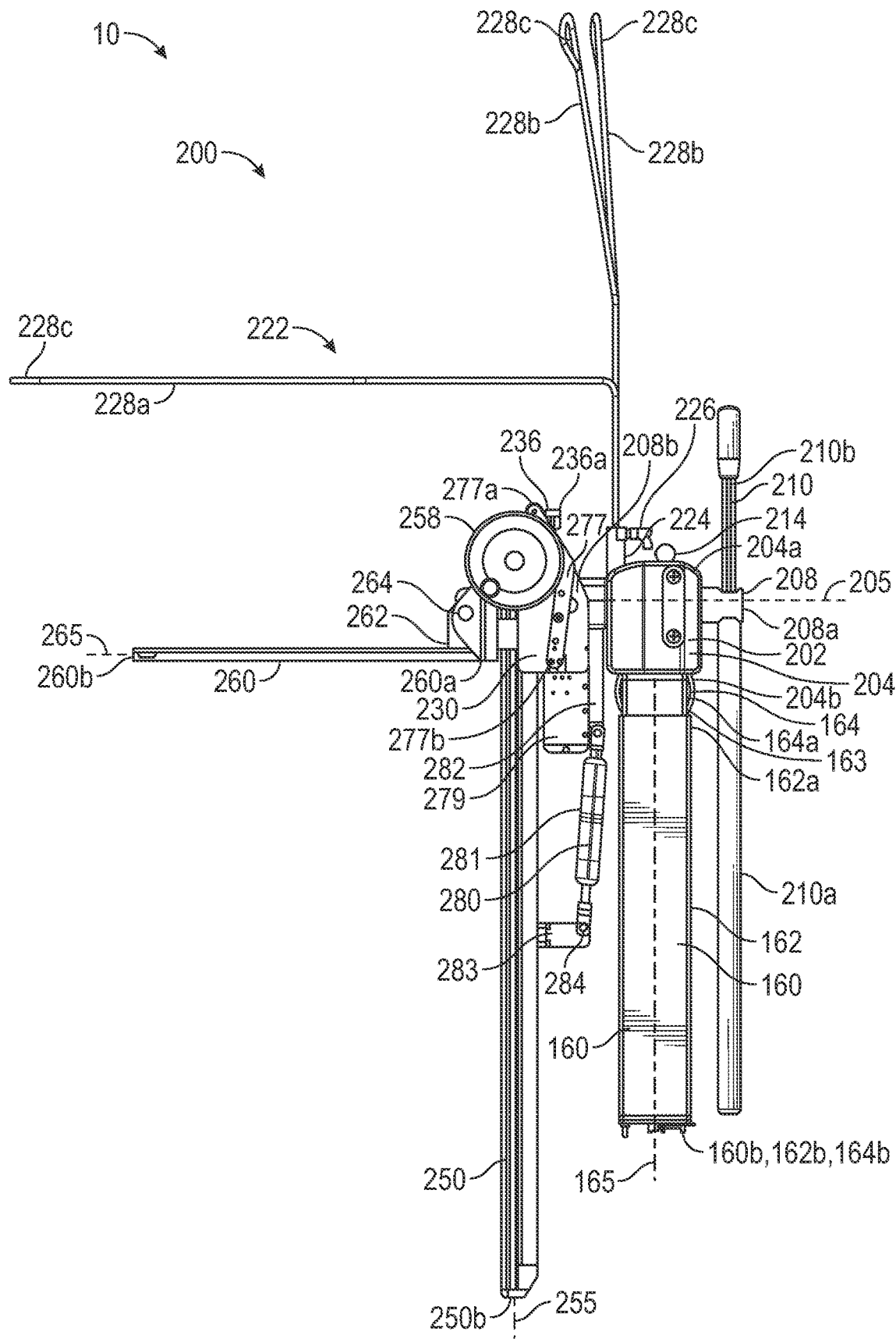
FIG. 12 is another side view of the rail assembly of FIG. 9.
Figure 13:
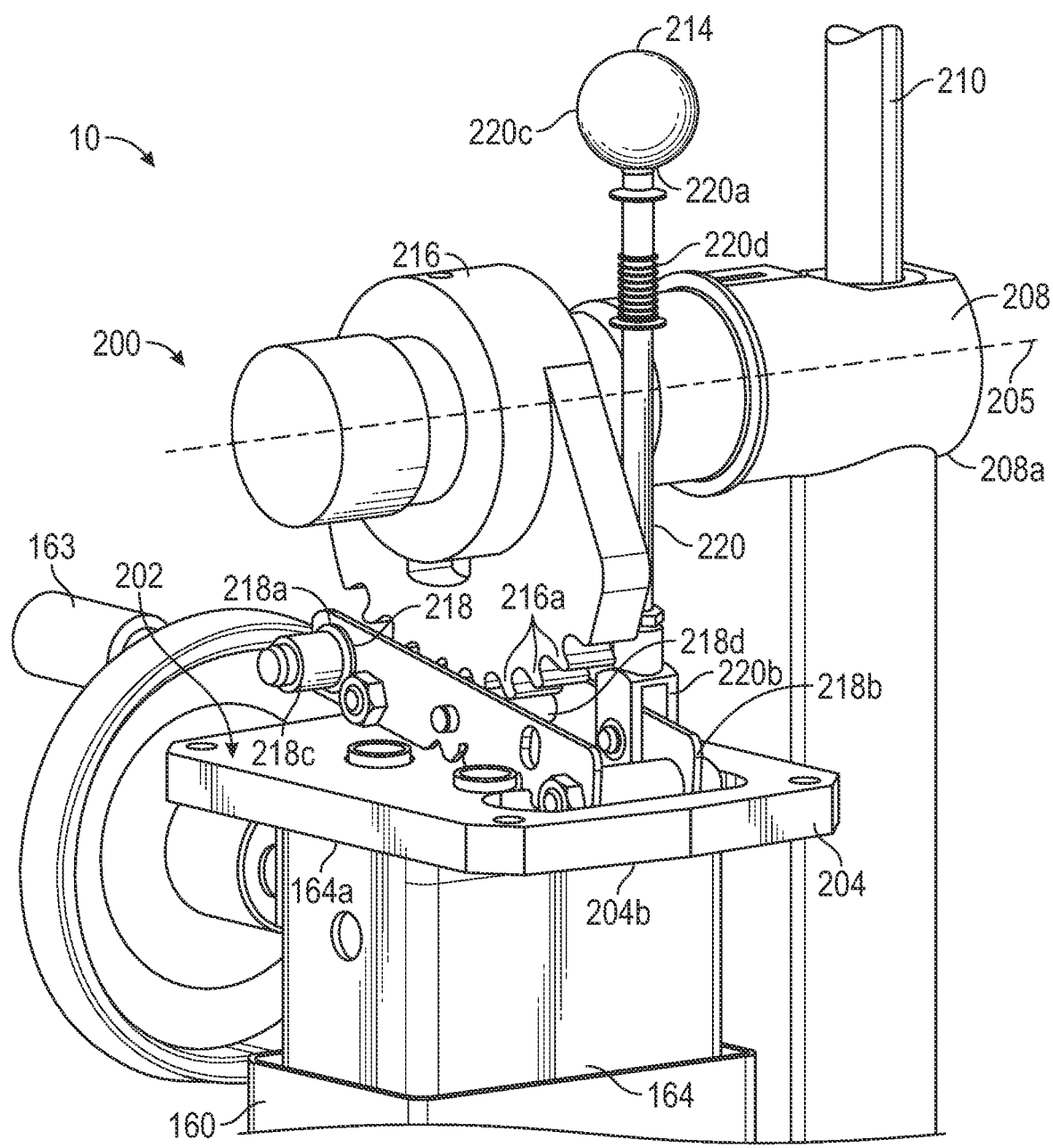
FIG. 13 is a perspective view of the locking apparatus of the rail assembly of FIG. 9.

Referring briefly to FIGS. 11-13, in this embodiment, handle 210 is extendable (i.e., has a length that can be varied). In particular, handle 210 includes a tubular outer handle 210a that extends generally downward from end 208a of shaft 208 and an inner handle 210b disposed slidingly disposed within outer handle 210a. Thus, inner handle 210b can be telescopically extended from and retracted into outer handle 210a. Inner handle 210b is biased by gravity to a retracted position substantially disposed within outer handle 210a. It should be appreciated that by extending handle 210b from outer handle 210a, the operator of system 10 has greater leverage to apply torque to shaft 208 (i.e., a larger moment arm). Thus, unless needed for applying additional torque to shaft 208, inner handle 210b is generally disposed within outer handle 210a and will not obstruct an operator attempting to operate other components of system 10. Outer handle 210a has a length sufficient to receive substantially the entire length of inner handle 210b. Due to the length of outer handle 210 extending towards the ground, the operator of system 10 can also apply rotational torque to shaft 108 by acting on outer handle 210a with the operator's leg, knee, or foot. In this manner, the operator may apply substantial torque to shaft 208 without needing to actuate handle 210 using the operator's hands. As will be described in more detail below, carrier 230 can be controllably pivoted about axis 213 in either direction independent of the rotation of shaft 208 and carrier 230 about axis 205. Thus, in this embodiment, carrier 230 can be controllably pivoted relative to base 202 and post assembly 160 about two separate axes 205, 213. Axis 205 lies in a horizontal plane oriented perpendicular to axis 165 of post assembly 160, and axis 213 lies in a vertical plane oriented perpendicular to axis 205. Therefore, in top view (shown in FIG. 10), axes 205, 213 are perpendicular. Shaft 208, and hence carrier 230, can be rotated in either direction about axis 205 relative to base 202, and carrier 230 can be rotated in either direction about axis 213.

Referring now to FIGS. 13-15, locking apparatus 214 releasably locks the rotational/angular position of shaft 208, and hence carrier 230, about axis 205 relative to housing 204 and support assembly 100. In other words, locking apparatus 214 has an "unlocked" position (shown in FIGS. 13-15) allowing rotation of shaft 208 about axis 205, and a "locked" position preventing the rotation of shaft 208 about axis 205. Regardless of whether locking apparatus 214 is in the locked or unlocked position, carrier 230 can pivot freely about axis 213 of pin 212. In this embodiment, locking apparatus 214 includes a cam sleeve 216 fixably mounted to shaft 208 between ends 208a, 208b, a rocker arm 218 pivotally coupled to housing 204, and a locking lever 220 for controllably pivoting arm 218 relative to housing 204 and cam sleeve 216. The lower end of cam sleeve 216 includes a plurality of circumferentially spaced teeth 216a, each tooth 216a being disposed at the same radius from axis 205. Rocker arm 218 has a first end 218a pivotally coupled to housing 204 at a pivot point 218c and a second end 218b opposite first end 218a. Thus, end 218b of rocker arm 218 can be pivoted up and down about end 218a and a horizontal axis extending through pivot point 218c. A rocker arm 218 also includes a locking member 218d positioned between ends 218a, 218b. Locking member 218d is sized and positioned to releasably engage a pair of circumferentially adjacent teeth 216a of cam sleeve 216. Engagement of locking member 218d with teeth 216a prevents rotation of shaft 208, and disengagement of locking member 218d and teeth 216a allows rotation of shaft 208. Thus, locking apparatus 214, rocker arm 218, and locking member 218d have a "locked" position with member 218d engaging adjacent teeth 216a and an "unlocked" positioned with member 218d disengaged and spaced from teeth 216a. As will be described in more detail below, in this embodiment, locking member 218d is biased upward into engagement with teeth 216a, and thus, locking apparatus 214, rocker arm 218, and locking member 218d are biased to the locked position.

Locking lever 220 transitions locking apparatus 214, rocker arm 218, and locking member 218b from the locked position to the unlocked position. In particular, locking lever 220 has a first or upper end 220a extending vertically from upper end 204a of housing 204 and a second or lower end 220b pivotally coupled to rocker arm 218 proximal second end 218b. Upper end 220a comprises a knob 220c that can be grasped by the operator of system 10 to actuator locking apparatus 214. Thus, the operator can press knob 220c downward to pivot rocker arm 218 about point 218c and rotate locking member 218d downward out of engagement with teeth 216a, thereby unlocking shaft 208. A spring return 220d disposed about lever 220 biases lever 220 upward, thereby biasing locking member 218d upward into engagement with teeth 216a.

Referring now to FIGS. 9-12, 16, and 17, a locking pin 236 releasably locks carrier 230 relative to pin 212. As will be described in more detail below, locking pin 236 has a "locked" position preventing carrier 230 from rotating about axis 213 and an "unlocked" position allowing carrier 230 to rotate freely about axis 213. A balancing assembly 280 applies a balancing force on first rail 250, and hence a balancing torque on carrier 230, to balance the weight of rail 260, foot holder assembly 300 and the patient's leg once it is strapped into foot holder assembly 300 and locking pin 236 is transitioned to the unlocked position. In particular, the weight of rail 260, assembly 300, and the patient's affected leg provide a first moment or torque on carrier 230 in a first rotational direction 231 at least partially defined by the distance of their collective center of mass from axis 213 of carrier 230. To balance against this first torque on carrier 230 when pin 236 is unlocked, balancing assembly 280 provides a second moment or torque on carrier 230 in a second direction 233 opposite direction 231. Thus, balancing assembly 280 is configured to counterbalance or substantially counterbalance the first moment (i.e., torque applied to carrier 230 by the weight of rail 260, assembly 300, and the patient's affected leg). Thus, when pin 236 is unlocked, very little to no force or torque needs to be applied to carrier 230 to overcome the weight of rail 260, foot holder assembly 300, and the patient's leg in order to rotate carrier 230 about axis 213 in second direction 233. As a result, carrier 230 is generally free to "follow" the leg of the patient coupled to foot holder assembly 300, such that the patient or operator of system 10 may easily adjust the position of the patient's affected leg without the need to apply substantial force or torque.

Figure 17:
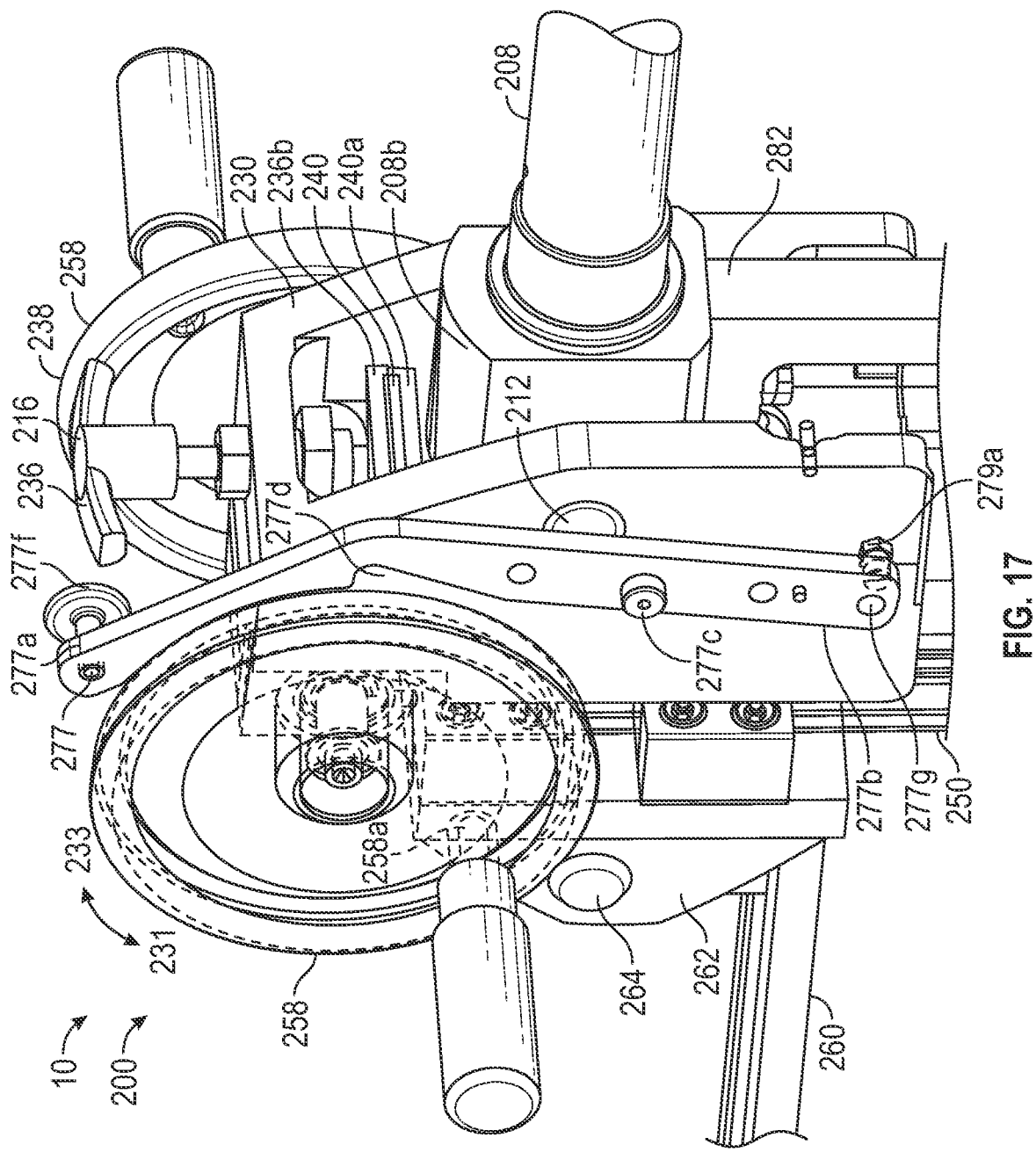
FIG. 17 is an enlarged partial perspective view of the rail assembly of FIG. 9.
Figure 18:
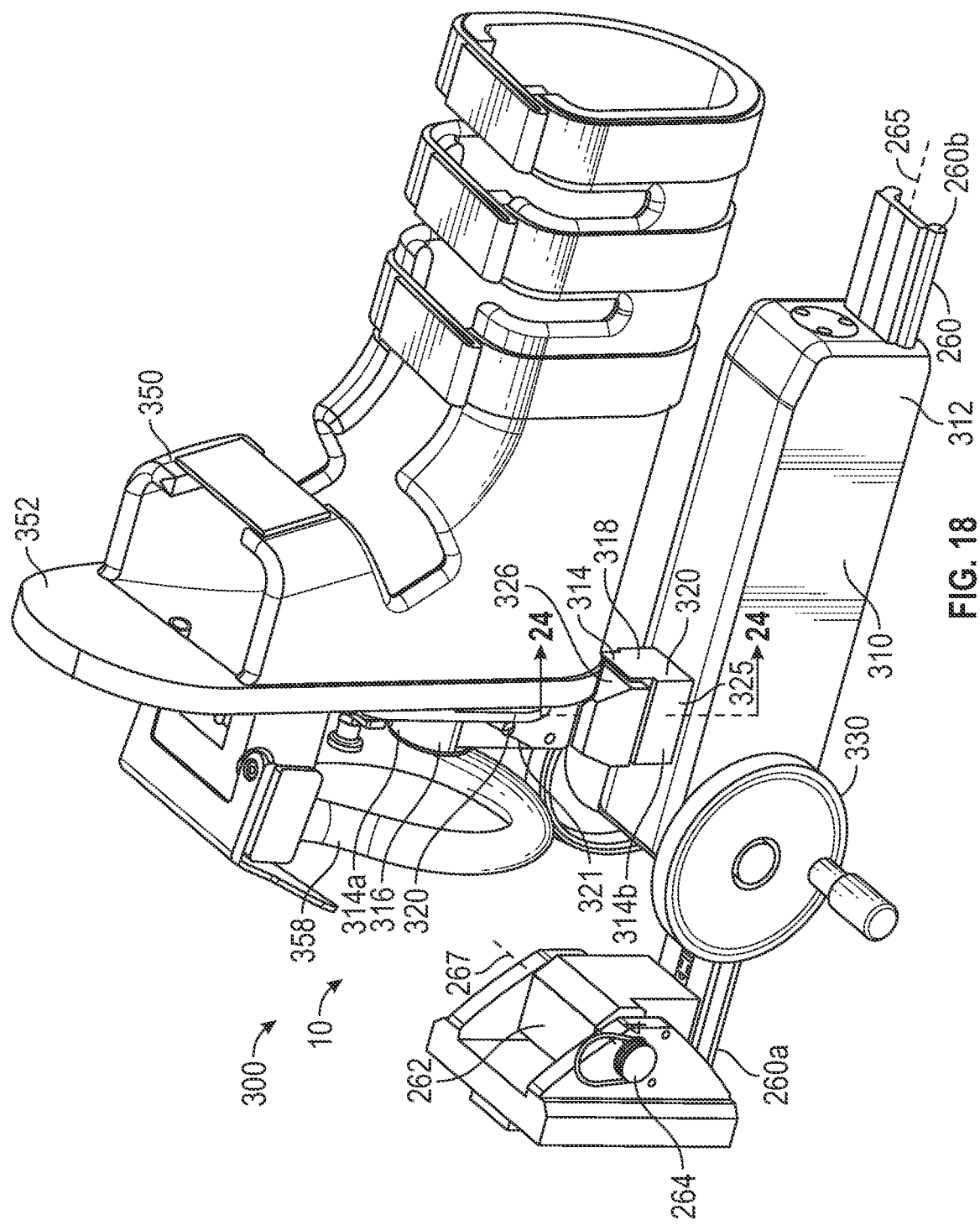
FIG. 18 is a perspective view of a foot holder assembly of the system of FIG. 1.
Figure 19:
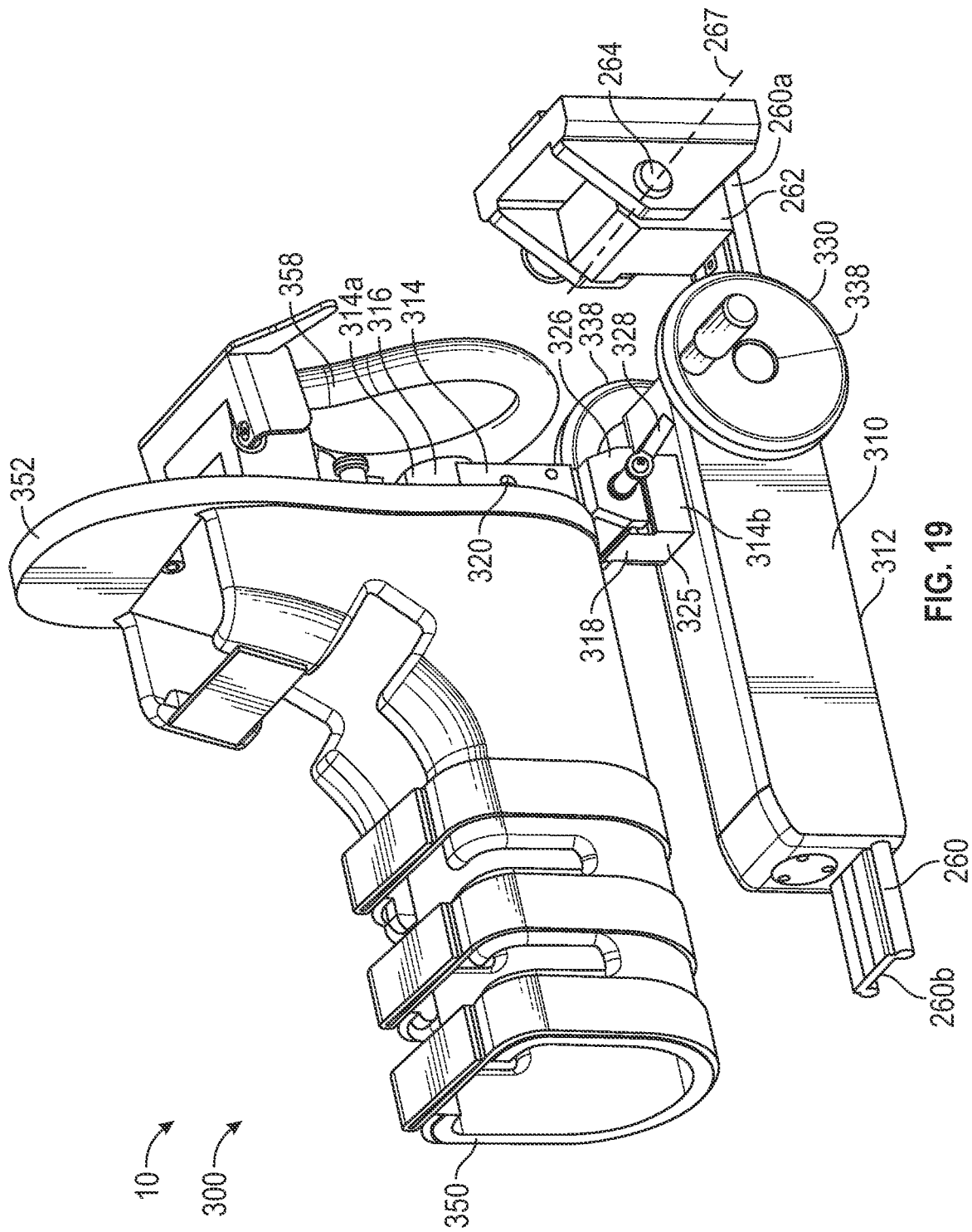
FIG. 19 is another perspective view of the foot holder assembly of FIG. 18.
Figure 20:
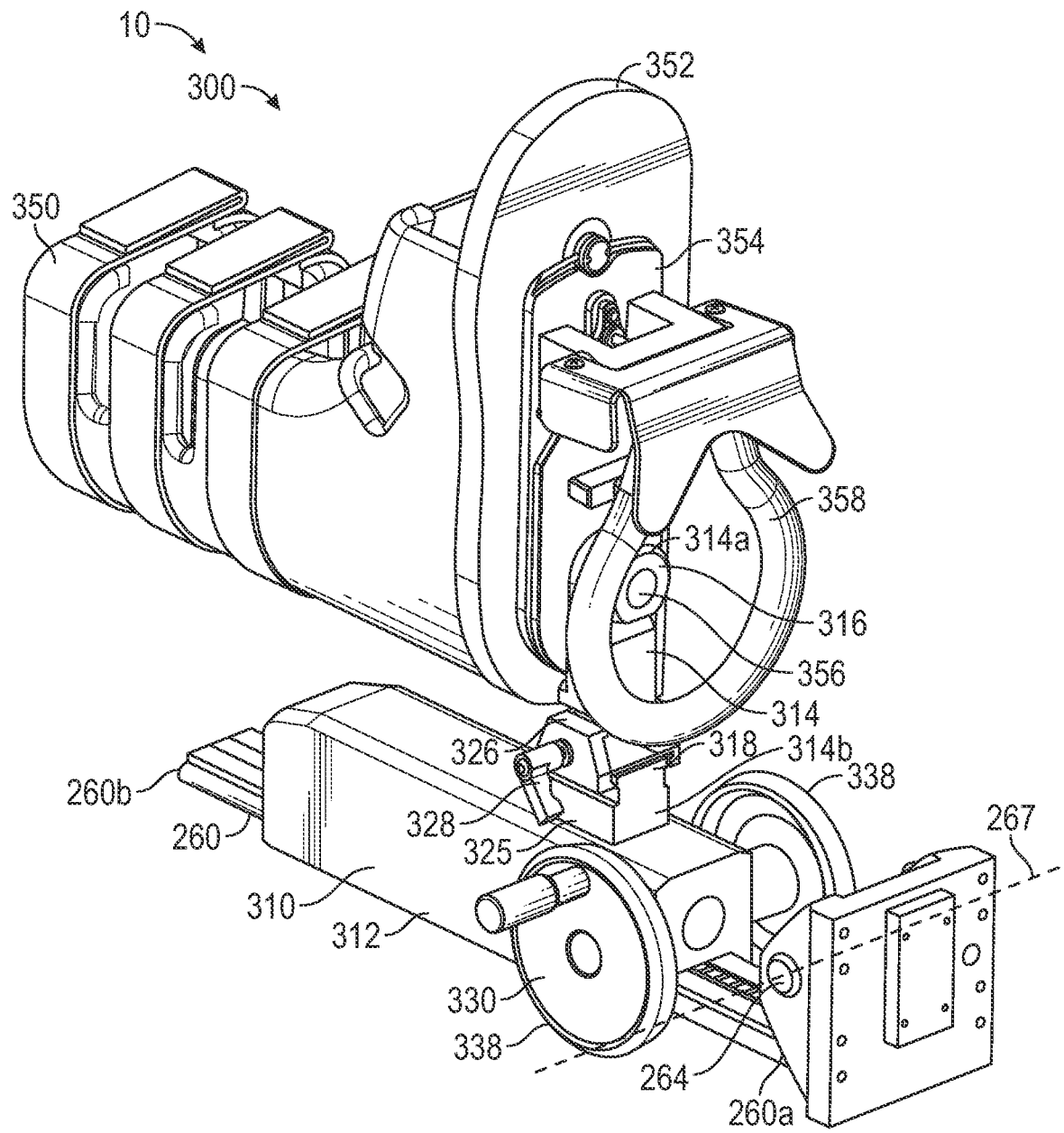
FIG. 20 is another perspective view of the foot holder assembly of FIG. 18.
Figure 21:
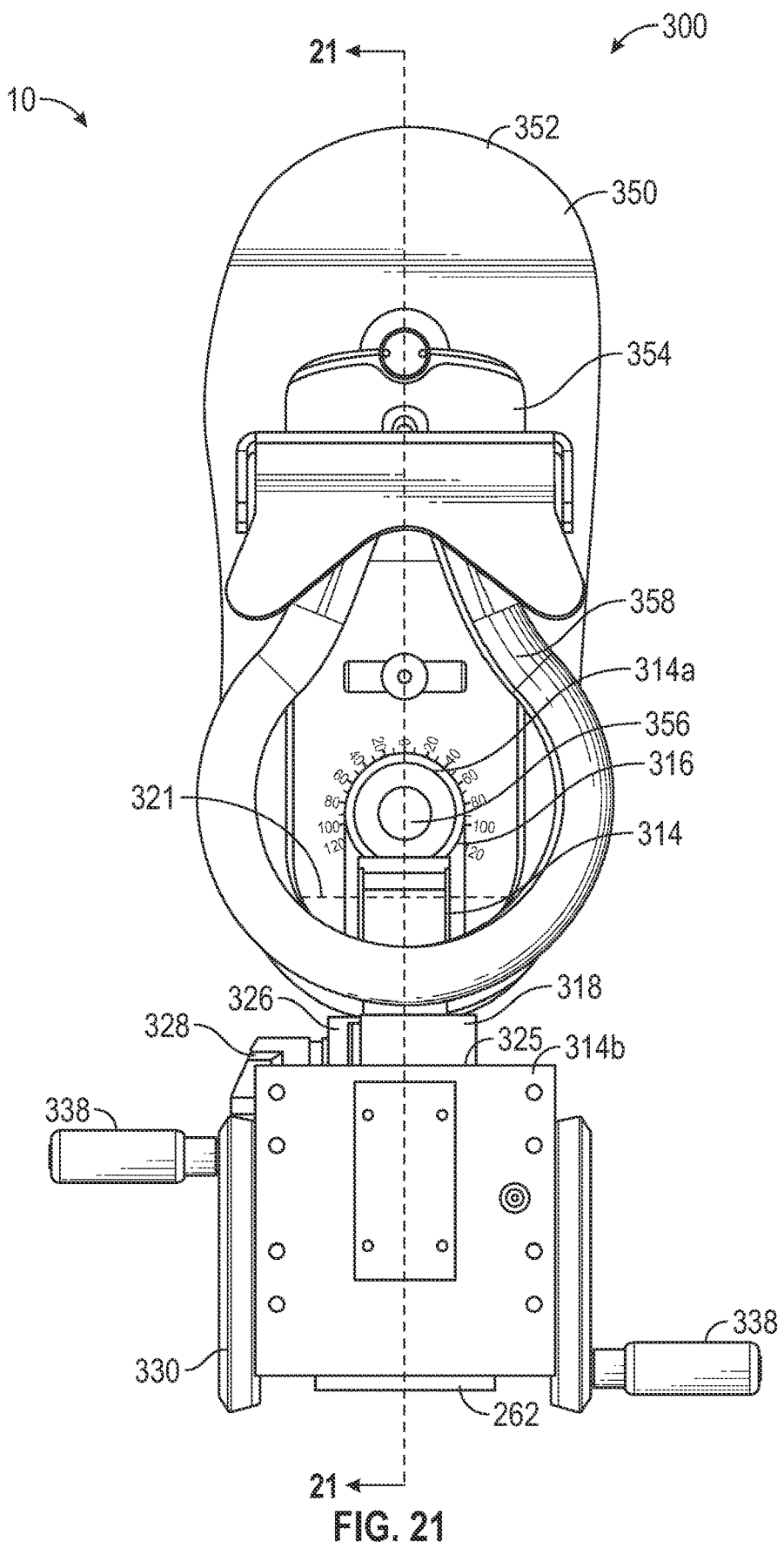
FIG. 21 is a front view of the foot holder assembly of FIG. 18.

Locking pin 236 is provided to selectively prevent carrier 230 from rotating downward in first direction 231 about axis 213, thereby releasably locking the rotational position of carrier 230 about axis 213. As best shown in FIGS. 16 and 17, in this embodiment, locking pin 236 includes a first or upper end 236a, a second or lower end 236b, a handle 238 disposed at upper end 236a for axially displacing locking pin 236, and an elongate engagement block or member 240 disposed at lower end 236b for selectively engaging the second end 208b of shaft 208. In particular, engagement member 240 includes a convex surface 240a configured to engage a mating concave recess 208c of shaft 208. Locking pin 236 has an "unlocked position" (shown in FIG. 16) with locking pin 236 displaced axially upwards using handle 238 to remove member 240 from recess 208c of shaft 208, thereby allowing free rotation of carrier 230 about axis 213 in either direction 231, 233; and a "locked" position with pin 236 displaced axially downwards and engagement member 240 seated in mating recess 208c of shaft 208, thereby preventing rotation of carrier 230 about axis 213 in either direction 231, 233.

Referring still to FIGS. 9-12 and 16, in this embodiment, balancing assembly 280 includes a hydraulic piston-cylinder damper 281, a first adapter 282 coupling damper 281 to shaft 208, and a second adapter 283 coupling damper 281 to first rail 250. Damper 281 has a central axis 285, a first or upper end 281a, and a second or lower end 281b. Ends 281a, 281b can move axially toward and away from each other, thereby axially contracting and extending damper 281. First adapter 282 has a first or upper end 282a fixably secured to shaft 208 between housing 204 and carrier 230 and a second or lower end 282b pivotally coupled to upper end 281a of damper 281 with a pinned connection 284. Second adapter 283 has a first end 283a fixably secured to first rail 250 distal carrier 230 and a second end 283b pivotally coupled to lower end 281ba of damper 281 with a pinned connection 284. As previously described, balancing assembly 280 balances the torque on carrier 230, to balance the weight of rail 260, foot holder assembly 300 and the patient's leg once it is strapped into foot holder assembly 300 and locking pin 236 is transitioned to the unlocked position. In addition, balancing assembly 280 dampens and smooths the rotation of carrier 230 about axis 213 in both rotational directions 231, 233. In particular, as ends 281a, 281b move axially relative to each other (extension and contraction), damper 281 dampens such movement, thereby slowing and smoothing the movement of ends 281a, 281b relative to each other, and hence, slowing and smoothing the rotation of carrier 230 about axis 213 in both rotational directions 231, 233.

Referring now to FIGS. 9, 11, 12, and 16, vertical guide rail 250 has a central or longitudinal axis 255, a first or fixed end 250a fixably coupled to block 232, and a second or free end 250b distal block 232. As shown in the cross-sectional view of FIG. 16, vertical guide rail 250 includes an outer rail 252, a flexible belt 254 (e.g., nylon belt, Kevlar belt, chain, etc.) disposed within rail 252, a sprocket 256 rotatably coupled to fixed end 250a, and a crank 258 fixably coupled to the sprocket 256. Guide rail 250 also includes a second sprocket (not shown) at free end 250b. Belt 254 engages and extends around first sprocket 256 and the second sprocket. Crank 258 is rotated (in either direction) to drive the rotation of sprocket 256, which is in turn moves belt 254 around the sprockets. In this embodiment, crank 258 is manually rotated by the operator of system 10; however, in other embodiments sprocket 256 may be driven by an actuator, such as a hydraulic actuator or an electric motor, etc. As will be described in more detail below, horizontal guide rail 260 is coupled to belt 254, and thus, as belt 254 moves around the sprockets, horizontal guide rail 260 moves axially (relative to axis 255) along guide rail 250. Crank 258 can be rotated in either direction to move horizontal guide rail 260 up or down along guide rail 250, as desired.

Displacement of horizontal guide rail 260 along rail 250 and rotation of crank 258 can be selectively locked via actuation of a locking member 277. Specifically, locking member 277 is configured to selectively and releasably prevent downward displacement of rail 260 along rail 250 via physical engagement between locking member 277 and a pin 258a (FIG. 17) of hand crank 258 that extends towards horizontal rail 260 along an axis parallel with axis 213. In this embodiment, locking member 277 is pivotally coupled to carrier 230 and includes a first or upper end 277a, a second or lower end 277b, and a pinned joint 277c pivotably or rotatably coupled to carrier 230. Pinned joint 277c defines an axis of rotation for locking member 277 that is parallel to axis 213. Locking member 277 includes a recess or notch 277d for releasably engaging pin 258a. In this embodiment, notch 277d is sized and shaped to prevent rotation of crank 258 in one direction, lowers rail 260 (generally parallel to first direction 231), when pin 258a is seated therein, but allows free rotation of crank 258 in the opposite direction (generally parallel to second direction 233) even when pin 258a is seated therein.

In this embodiment, upper end 277a of locking member 277 is biased forward toward pin 258a via a biasing member (not shown). Thus, when hand crank 258 is rotated in a direction parallel to direction 233 for a single revolution, pin 258a will slidingly engage locking member 277 and pass through notch 277d as it moves towards lower end 277b. However, when hand crank 258 is rotated in a direction parallel to direction 231 for a single revolution, pin 258a will slidingly engage locking member 277 as it moves toward upper end 277a, but will positively engage notch 277d, thereby restricting further rotation of hand crank 258 in the direction parallel to direction 231. In order to further rotate hand crank 258 in the direction parallel to direction 231, locking member 277 end 277a is pulled backward away from pin 258a (in a direction parallel to direction 233) from the locked position with pin 258a seated in notch 277d to the unlocked position (shown in FIG. 17) with notched 277d pulled away from pin 258a, thereby releasing pin 258a of crank 258. As previously described, locking member 277 and notch 277d are biased toward pin 258a, but can be pivoted to the unlocked position by pulling a knob 277f disposed at upper end 277a of locking member 277. In this manner, pin 258a of hand crank 258 will engage notch 277d of locking member 277 for each individual rotation of crank 258.

In this embodiment, locking member 277 interfaces with a radio frequency identification (RFID) lock 279 (hidden in FIG. 16), which is configured to selectably or releasably lock the angular or rotational position of locking member 277, thereby preventing rotation of hand crank 258 in either angular direction 231, 233. RFID lock 279 includes a retractable pin 279a that extends along an axis parallel with axis 213 and is configured to physically engage an indentation 277g that extends into locking member 277 at lower end 277b. In particular, pin 279a includes an unlocked position where pin 279a is retracted into RFID lock 279 and a locked position where pin 279a is axially extended into indentation 277g of locking member 277, thereby preventing rotation of locking member 277 about pinned joint 277c. RFID lock 279 is configured to transition between the unlocked and locked positions in response to an electromagnetic signal transmitted between lock 279 and an RFID tag, as are known in the art, configured to communicate with lock 279. The RFID lock 279 may be configured to transition between the locked position to the unlocked position for a predetermined period of time in response to the transmission of an electromagnetic signal between lock 279 and an RFID lock. RFID tags may also be configured to unlock RFID lock 279 a predetermined number of times.

Referring now to FIGS. 9-12 and 16-21, horizontal guide rail 260 has a central or longitudinal axis 265, a first end 260a pivotally coupled to guide rail 250, and a second or free end 260b distal vertical guide rail 250. First end 260a is pivotally coupled to a mounting block 262 with a pinned connection 264 that allows guide rail 260 to pivot relative to mounting block 262 about a horizontal axis 267. In particular, pinned connection 264 allows guide rail 260 to pivot upward about axis 267 from a default position oriented perpendicular to vertical guide rail 250 and pivot downward about axis 267 to the default position oriented perpendicular to vertical guide rail 250. In other words, guide rail 260 cannot rotate below the default position oriented perpendicular to guide rail 250. In this embodiment, guide rail 260 may pivot freely about axis 267 (i.e., there is no resistance to the rotation of guide rail 260 about axis 267). However, in other embodiments, the horizontal guide rail (e.g., guide rail 260) includes a locking mechanism to selectively and releasably lock pivoting of the horizontal rail relative to the vertical rail (e.g., rail 250).

Mounting block 262 is fixably secured to belt 254 of first guide assembly 250, and thus, as block 262 moves up and down relative to outer rail 252, horizontal guide rail 260 moves up and down relative to outer rail 252. In this embodiment, mounting block 262 is fixably secured to belt 254 with a clamp 272. Thus, by rotating the sprocket 256 via hand crank 258, belt 254 is advanced around sprocket 254 to displace mounting block 262 axially along vertical guide rail 250—when hand crank 258 is rotated in one direction, mounting block 262 moves toward end 250a of vertical guide rail 250, and rotation of sprocket 256 in the opposite angular direction moves mounting block 262 toward end 250b of guide rail 250. Once the desired position of mounting block 262 along vertical guide rail 250 is achieved, block 262 can be locked relative to guide rail 250 by locking belt 254 as previously described. Horizontal guide rail 260 supports foot holder assembly 300 (not shown in FIGS. 9-12), and allows foot holder assembly 300 to move axially along its length.

Referring now to FIGS. 18-24, foot holder assembly 300 includes a slide block or carriage 310 slidably mounted to guide rail 260 and a boot 350 pivotally coupled to carriage 310. A drive assembly 330 controllably moves carriage 310 axially (relative to axis 265 of rail 260) in either direction along guide rail 260 (i.e., toward end 260a or end 260b). In this embodiment, carriage 310 includes a housing 312 slidingly engaging guide rail 260 and a post 314 extending upward from housing 312. Post 314 has a first or upper end 314a pivotally coupled to boot 350 with a rotatable coupling 316, a second or lower end 314b coupled to housing 312 with a mount assembly 318, and a pivot joint assembly 320 disposed between ends 314a, 314b. Pivot joint assembly 320 includes a pivot joint 320a that allows end 314a, and hence boot 350 coupled thereto, to pivot freely relative to lower end 314b about an axis 321 disposed in a vertical plane oriented perpendicular to axis 265. In this embodiment, pivot joint 320a allows end 314a, and hence boot 350, to pivot about axis 321 relative to lower end 314b through a limited angle θ measured counterclockwise in FIG. 22 from a position with post 314 oriented perpendiculars to rail 260. Angle θ is preferably limited to 0° to 30°, where 0° corresponds to the position shown in FIGS. 18-22 with post 314 perpendicular to rail 260, and 30° corresponds to rotation 30° (from 0°) toward carrier 230.

Figure 24:
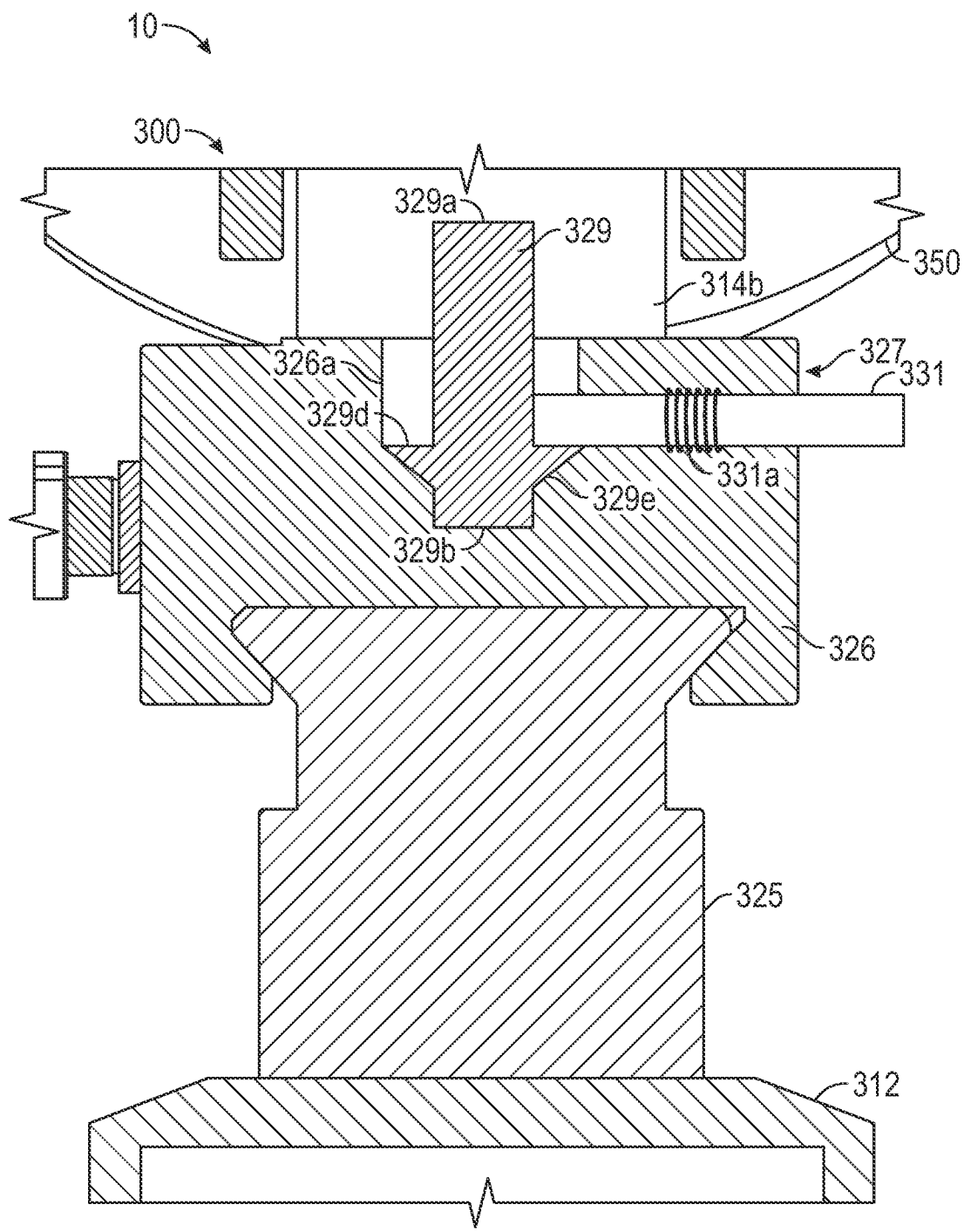
FIG. 24 is a cross-sectional view of the foot holder assembly of FIG. 18 taken along section 24-24 of FIG. 18.

Mount assembly 318 includes a fixed block 325 secured to the top of carriage 310, a slider block 326 slidably and releasably coupled to fixed block 325, and a quick release coupling 327 releasably coupling the lower end 314b of post 314 to slider block 326. Thus, two releasable connections are provided between boot 350 and carriage 310—the coupling between blocks 325, 326 and the quick release coupling 327 between post 314 and slide block 326. In this embodiment, blocks 325, 326 are releasably coupled with a sliding dovetail joint that allows slider block 326 to slide axially (parallel to axis 265). A manually operated lock 328 has an unlocked position allowing slider block 326 to be slid along fixed block 325 and a locked position preventing slider block 326 from moving relative to fixed block 325. Thus, with lock 328 in the unlocked position, block 326 can be moved along block 325 to the desired position, and then lock 328 transitioned to the locked position preventing relative movement between blocks 325, 326. As best shown in FIG. 24, quick release coupling 327 includes a pin 329 received within a mating receptacle 326a in the top of slider block 326 and a locking pin 329 that releasably locks pin 329 within receptacle 326a. When pin 329 is disposed in receptacle 326a, pin 329 and hence boot 350 can rotate freely about the central axis of pin 329 relative to slider block 326, fixed block 325, and carriage 310. Pin 329 has a first or fixed end 329a fixably secured to lower end 314b of post 314, a second or free end 329b opposite end 329a, and a radially extending flange 329c disposed between ends 329a, 329b. Flange 329c has a planar upper surface 329d and a frusto-conical or tapered lower cam surface 329e. Locking pin 331 extends through slider block 326 into receptacle 326a. In this embodiment, the inner end of pin 331 is biased into receptacle 326a with a biasing member 331a (e.g., a coil spring). To make up quick release coupling 327, thereby coupling boot 350 to carriage 310 and rail 260, pin 329 is inserted into receptacle 326a. Cam surface 329e slides along the inner end of locking pin 331 disposed in receptacle 326a and pushes locking pin 331 outward, thereby allowing pin 329 to be fully seated in receptacle 326a. Once flange 329c is disposed below locking pin 331, biasing member 331a pushes locking pin 331 back into receptacle 326a, thereby preventing pin 329 from being pulled out of receptacle 326a while allowing pin 329 to rotate therein. To remove pin 329 from receptacle 326a, thereby decoupling boot 350 from carriage 310 and rail 260, locking pin 331 is pulled outward so its inner end no longer engages flange 329c, and then pin 329 is pulled from receptacle 326a.

Figure 22:
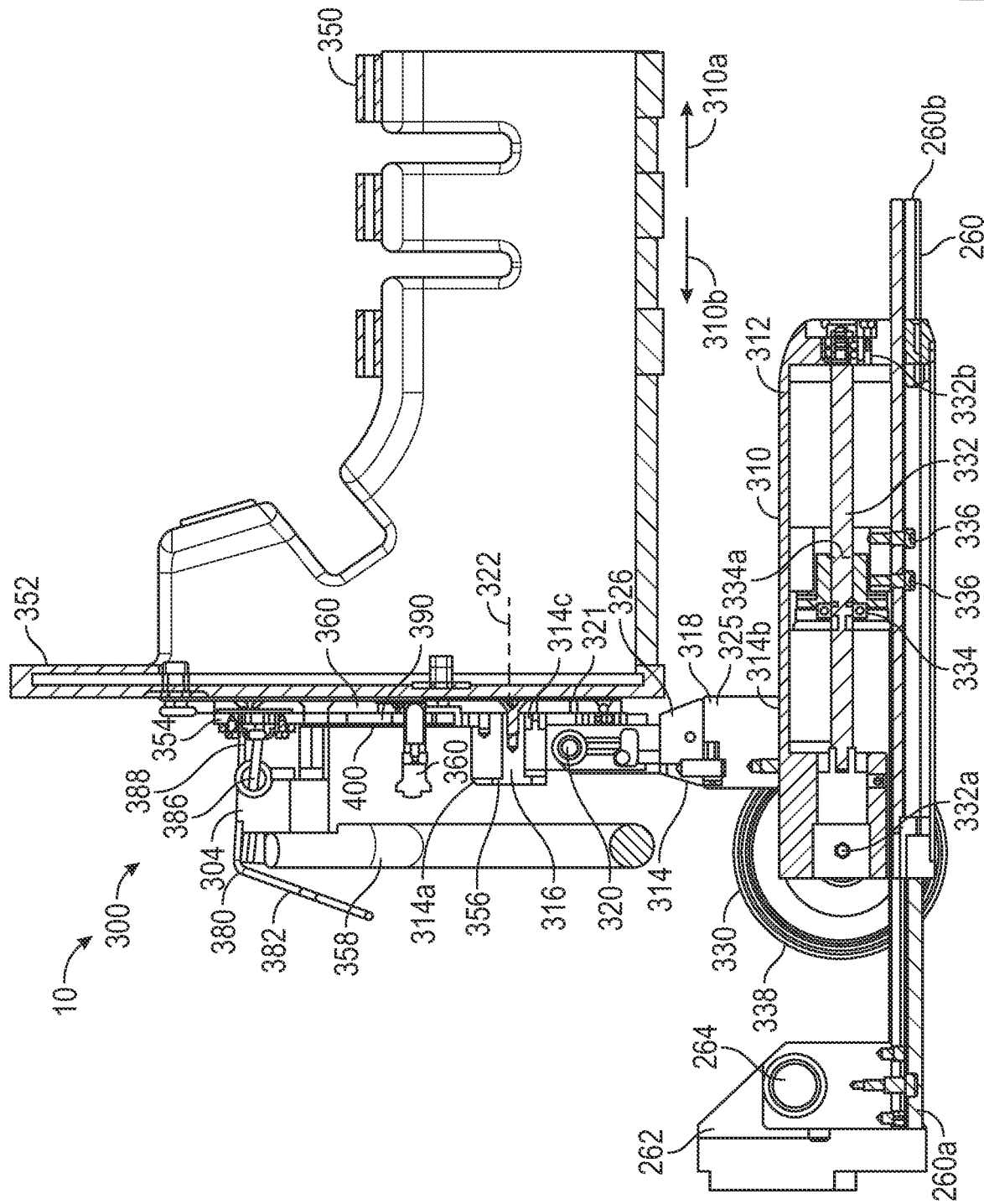
FIG. 22 is a cross-sectional view of the foot holder assembly of FIG. 18 taken along section 22-22 of FIG. 21.

As best shown in FIG. 22, in this embodiment, drive assembly 330 includes a drive screw or spindle gear 332 rotatably disposed within housing 312 and a drive block housing 334 disposed within housing 312. Drive block housing 334 is fixably secured to guide rail 260 with bolts 336 such that drive block housing 334 cannot move relative to rail 260. However, as will be described in more detail below, housing 312 can be moved axially along rail 260 relative to drive block housing 334.

Figure 23:
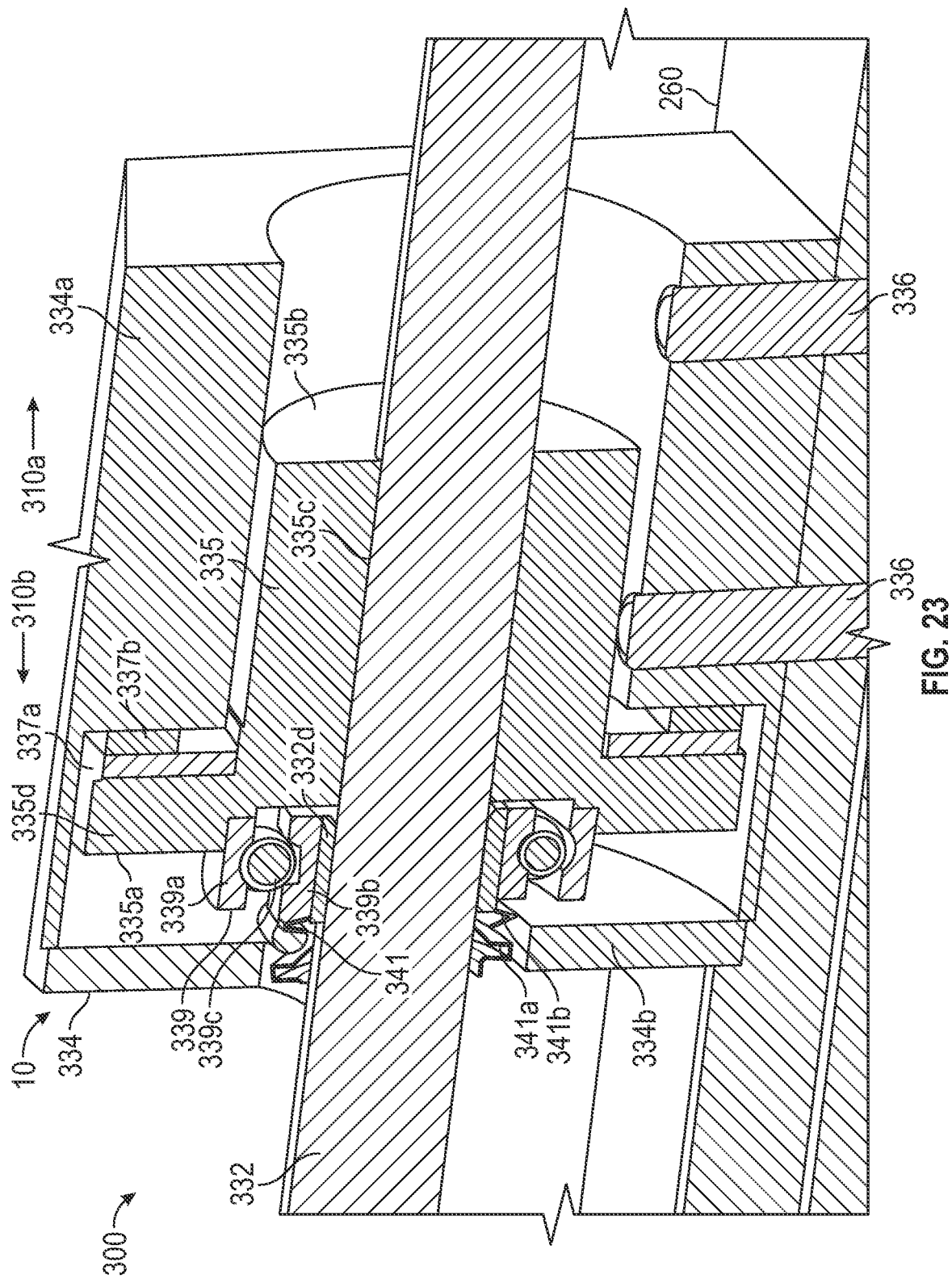
FIG. 23 is an enlarged partial perspective view of the cross-sectional view of FIG. 22 of the foot holder assembly of FIG. 17.

Referring now to FIGS. 22 and 23, spindle gear 332 extends axially (parallel to axis 265) through housing 312 and has a first end 332a rotatably coupled to a first end 312a of housing 312 and a second end 332b rotatably coupled to a second end 312b of housing 312. Thus, spindle gear 332 can rotate relative to housing 312 but cannot move axially relative to housing 312. In other words, spindle gear 332 and housing 312 move axially (relative to axis 265) together. The cylindrical outer surface of spindle gear 332 comprises external threads. In this embodiment, a hand crank 338 (FIGS. 18-21) is coupled to spindle gear 332 and can be used to manually rotate spindle gear 332. In other embodiments, different actuation means can be provided to rotate the spindle gear (e.g., spindle gear 332) such as an electric motor.

Referring still to FIGS. 22 and 23, a spindle 335 is slidably received in drive block housing 334 and threadably coupled to spindle gear 332. In particular, spindle 335 has a first end 335a proximal an end wall 334b of housing 334, a second end 335b opposite the first end 335a, and an internally threaded bore 335c extending axially (parallel to axis 265) between ends 335a, 335b. Spindle gear 332 extends through bore 335c of spindle 335 and housing 334, and has external threads that mate and engage internal threads in bore 335c. Thus, relative rotation between spindle 335 and spindle gear 332 causes spindle 335 and spindle gear 332 to move axially (parallel to axis 265) relative to each other.

Spindle 335 includes an annular flange 335d at first end 335a that extends radially outward and housing 334 includes an annular shoulder 334a axially opposed flange 335d. A pair of annular washers 337a, 337b are disposed about spindle 335 and axially positioned (relative to axis 265) between flange 335d and shoulder 334a. As will be described in more detail below, frictional engagement between flange 335d, washers 337a, 337b, and shoulder 334a allows the transfer of torque between spindle 335 and drive block housing 334.

A ball bearing 339 is disposed within drive block housing 334 about spindle gear 332. Bearing 339 includes a radially outer race 339a engaging spindle 335, a radially inner race 339b disposed within outer race 339a, and a plurality of circumferentially-spaced balls 339c rotatably disposed between races 339a, 339b. Balls 339c generally allow races 339a, 339b to rotate freely relative to each other. An annular slip or slide ring 332d is radially positioned between bearing 339 and spindle gear 332. Ring 332d slidingly engages spindle gear 332. In particular, ring 332d has a smooth cylindrical inner surface disposed at a diameter greater than or equal to the outermost reaches of the external threads of spindle gear 332 such that ring 332d contacts but is free to slide axially over spindle gear 332 and the external threads thereon. Outer race 339a radially abuts and is seated against an inner cylindrical surface of spindle 335 at first end 335a such that outer race 339a and spindle 335 do not move relative to each other. An annular biasing member 341 is also disposed within drive housing 334 about spindle gear 332. Biasing member 341 is axially positioned between end wall 334b of housing 334 and inner race 339b, and generally urges bearing 339, spindle 335, and washers 337a, 337b axially (parallel to axis 265) away from end wall 334b of housing 334, thereby biasing flange 335d axially against washers 337a, 337b, which in turn are biased against shoulder 334a of housing 334. Spindle gear 332 can be rotated in either direction about its central axis with crank 338 to move carriage 310, and hence boot 350 coupled thereto, axially back and forth along rail 260.

In particular, the axial force applied by biasing member 341 generates frictional loads between flange 335d and shoulder 334a (via washers 337a, 337b) that restrict and/or prevent relative rotation therebetween. In other words, frictional engagement between flange 335d of spindle 335, washers 337a, 337b, and shoulder 334a due to biasing member 341 maintains spindle 335 rotationally stationary relative to drive block housing 334 as spindle gear 332 rotates therein. As a result of the threaded engagement of spindle gear 332 and spindle 335, rotation of spindle gear 332 in a first direction relative to spindle 335 and housing 334 causes carriage 310 to move in a first axial direction 310a (toward end 260b and away from end 260a) and rotation of spindle gear 332 in a second direction relative to spindle 335 and housing 334 causes carriage 310 to move in a second axial direction 310b (toward end 260a and away from end 260b). Slip ring 332d slidingly engages spindle gear 332 and allows spindle gear 332 to move axially therethrough as spindle gear 332 rotates to move carriage 310 axially along rail 260. In this manner, crank 338 can be used to adjust the axial position of carriage 310, and boot 350 coupled thereto, along rail 260.

In this embodiment, drive assembly 330 also allows for one-way gross axial adjustment in the second axial direction 310b (toward end 260a). In particular, application of an axial tensile load to spindle gear 332 parallel to second axial direction 310b, such as by pulling on boot 350 or a handle attached thereto, pulls spindle gear 332 in the second direction 310b, urges flange 335d in the second axial direction 310b away from shoulder 334a, and urges bearing 339 in the second axial direction 310b, which axially compresses biasing member 341. The urging of flange 335d in the second axial direction 310b away from shoulder 334a reduces the frictional loads between flange 335d, washers 337a, 337b, and shoulder 334a, which enables spindle 335 to rotate relative to spindle gear 332 and housing 334 as the external threads of spindle gear 332 are pulled through spindle 335. Thus, as spindle gear 332 is pulled in second direction 310b through spindle 335, frictional loads between flange 335d, washers 337a, 337b, and shoulder 334a are reduced, which in turn allow the engagement of mating threads between spindle gear 332 and spindle 335 to induce free rotation of spindle 335 relative to housing 334 and spindle gear 332. Slip ring 332d slidingly engages spindle gear 332 and allows spindle gear 332 to move axially therethrough as it is pulled in second direction 310b. In the manner described, the axial position of boot 350 along rail 260 can be adjusted in either direction 310a, 310b by rotation of hand crank 338, and further, the axial position of boot 350 along rail 260 can be adjusted in second axial direction 310b by applying an axial force in second axial direction on boot 350. The former (i.e., rotation of spindle gear 332 via crank 338) is generally preferred for fine adjustment of the axial position of boot 350 in either direction 310a, 310b along rail 260, whereas the later (i.e., pulling of boot 350 in the second axial direction) is generally preferred for gross movement of boot 350 in the second axial direction 310b. It should be appreciated that the manual pulling of bot 350 in the second axial direction 310b can be used to apply traction to the patient's leg while simultaneously providing some feel or feedback to the operator of system 10 as to the degree of traction applied.

Referring now to FIGS. 18-22, boot 350 is configured to support and releasably retain a patient's foot and ankle. Boot 350 includes a rigid sole 352, and preferably includes straps, belts, snaps or other similar devices for securing a patient's foot therein. In this embodiment, boot 350 comprises a sterilizable, non-porous shell having sterile padding silicon straps to secure the foot within boot 350 and withstand traction forces applied to the patient's affected leg.

Figure 25:
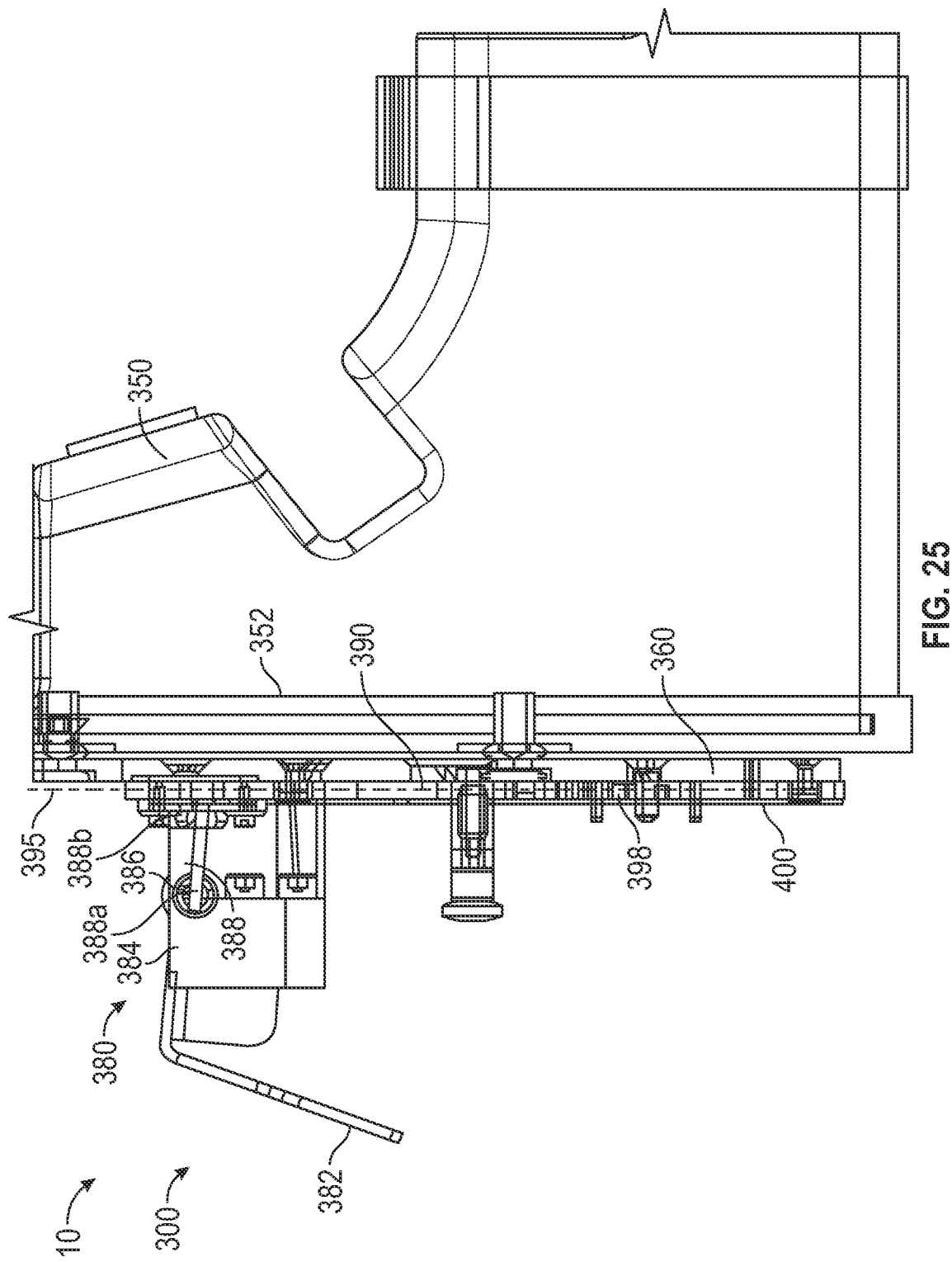
FIG. 25 is an enlarged partial view of the cross-sectional view of FIG. 22.
Figure 26:
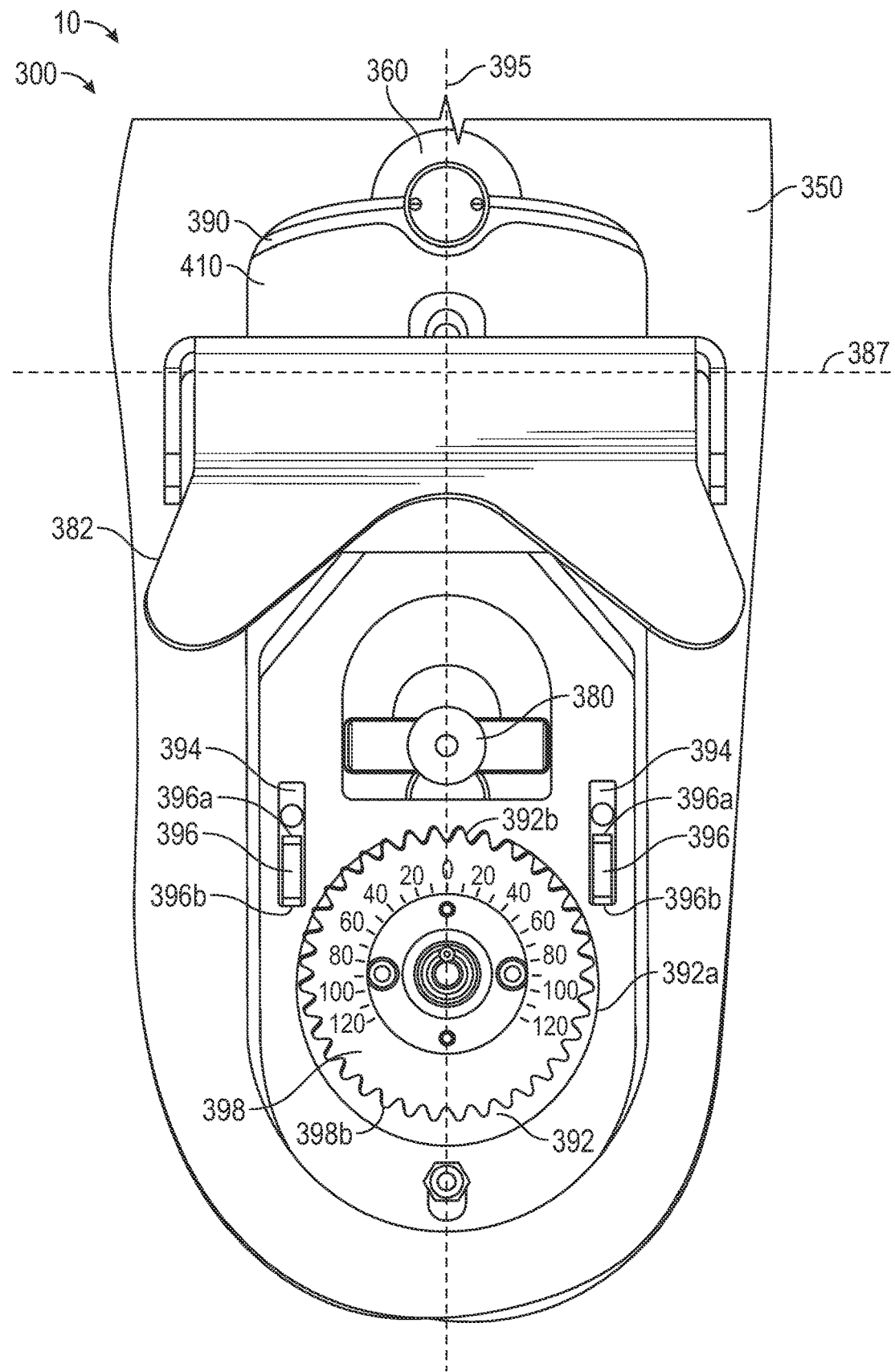
FIG. 26 is an enlarged partial front view of FIG. 21.
Figure 27:
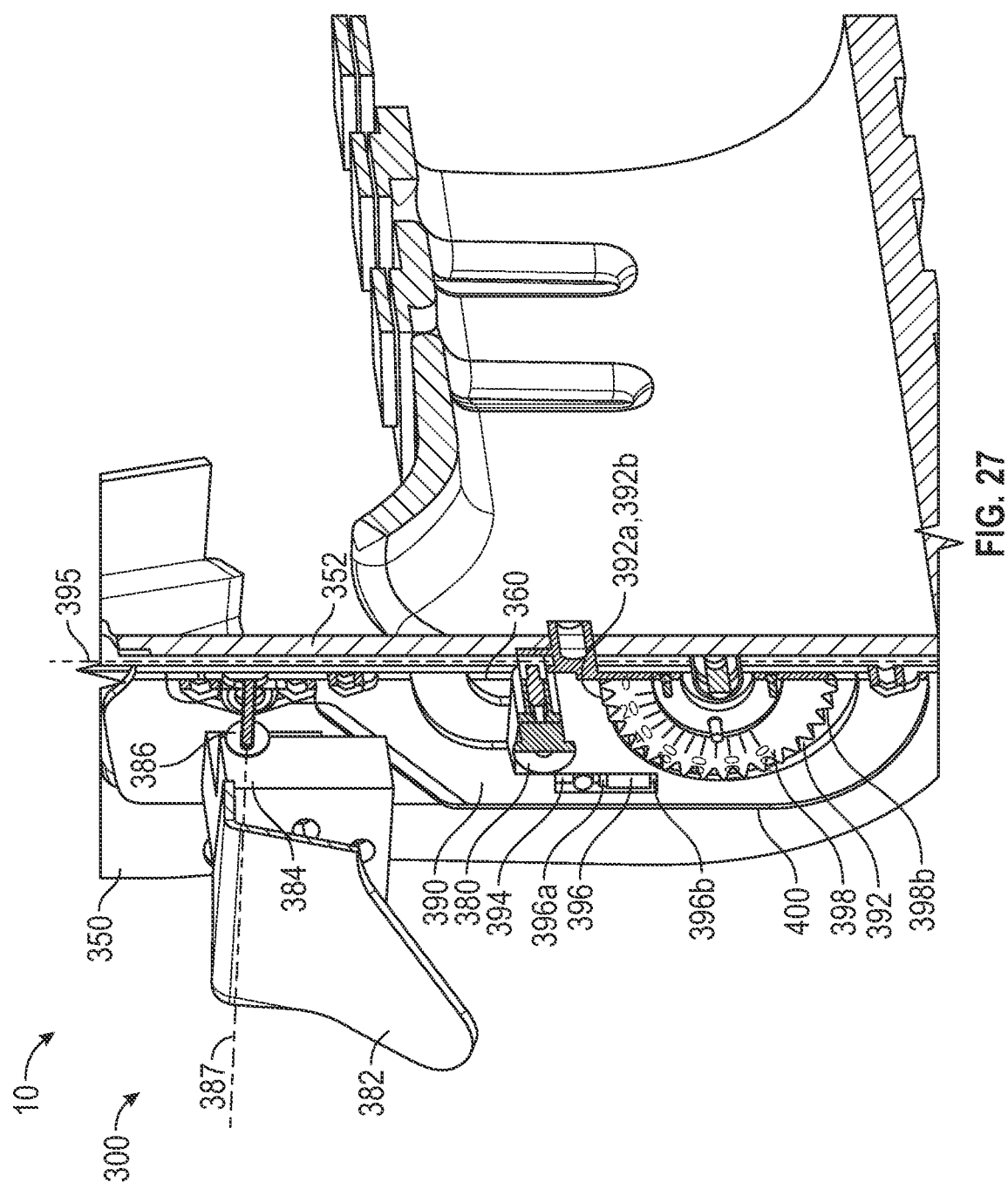
FIG. 27 is an enlarged partial perspective view of the cross-sectional view of FIG. 22.

The heel portion of rigid sole 352 is rotatably coupled to upper end 314a of post 314 with rotatable coupling 316. Thus, boot 350 can be controllably rotated in either direction about central axis 322 of coupling 316. In this embodiment, coupling 316 includes a rigid inner boot plate 360 immediately adjacent and affixed to rigid sole 352, a generally cylindrical shaft 356 extending perpendicularly from inner plate 360, and a through bore 314c in the upper end 314a of post 314. Shaft 356 is rotatably disposed in bore 314c such that shaft 356, plate 360, and boot 350 can be rotated about axis 322 relative to post 314. A bearing, bushing, rollers, etc. can be disposed in bore 314c between shaft 356 and pivot arm 314 to facilitate the smooth rotation of shaft 356 relative to pivot arm 314. Axis 322 is coaxially aligned with the central axis of shaft 356 and oriented to be generally aligned with and parallel to the patient's tibia when the patient's foot is secured in boot 350. A handle 358 is fixably attached to boot plate 360 and is used by the users of system 10 to permit manipulation of boot 350 about axes 322, 321. Handle 358 may also be utilized to apply gross traction to the patient's affected leg by exerting an axial force on handle 358 in the second direction 310b previously described to pull spindle gear 332 and housing 312 in the second direction 310b. Referring now to FIGS. 25-27, boot 350 further comprises a release mechanism 380 that releasably locks the rotation of boot 350 about axis 322. In particular release mechanism 380 has a "locked" position preventing rotation of boot 350 about axis 322 in either direction and an unlocked position allowing rotation of boot 350 about axis 322 in either direction. In this embodiment, release mechanism 380 is biased to the locked position, but can be transitioned to the unlocked position via physical actuation of release mechanism 380. In this embodiment, release mechanism 380 includes an intermediate plate 390 moveably coupled to inner plate 360, a cover plate 400 disposed over at least a portion of intermediate plate 390, and a rotatable handle or paddle 382 pivotably coupled to a support member 384 attached to outer plate 390. For purposes of clarity, cover plate 400 is hidden (i.e., not shown) in FIGS. 26 and 27.

Intermediate plate 390 has a central or longitudinal axis 395 and is moveably positioned between plates 360, 400. In addition, intermediate plate 390 includes a generally circular aperture 392 coaxially aligned with axes 395, 322 and a pair of elongate apertures 394 oriented parallel to axis 395. Apertures 394 are disposed on opposite sides of axis 395. A biasing member 396 is disposed in each aperture 394. Each biasing member 396 has a first or upper end 396a coupled to inner plate 356 and a second or lower end 396b coupled to intermediate plate 390 at the bottom of the corresponding elongate aperture 394. Circular aperture 392 has a radially inner surface 392a comprising a plurality of uniformly circumferentially-spaced teeth 392b along its upper portion. A dial 398 is fixably attached to upper end 314a of post 314 and disposed in aperture 392. Shaft 356 extends coaxially through dial 398, which includes a plurality of uniformly circumferentially-spaced teeth 398b disposed along its outer periphery. Teeth 398b of dial 398 are sized and shaped to releasably engage and interlock with teeth 392b of aperture 392. Thus, when teeth 392b positively engage teeth 398b, intermediate plate 390 and boot 350 are prevented from rotating about axis 322, however, when teeth 392b, 398b are disengaged, intermediate plate 390 and boot 350 can be freely rotated about axis 322. Thus, release mechanism 380 is disposed in the locked position when teeth 392b, 398b engage one another and is disposed in the unlocked position when teeth 392b, 398b are disengaged. In this embodiment, biasing members 396 bias teeth 392b into engagement with teeth 398b, thereby biasing release mechanism 280 to the locked position.

Paddle 382 is used to transition release mechanism 380 to the unlocked position by moving intermediate plate 390 axially relative to plates 360, 400. In particular, paddle 382 is pivotably coupled to support 384 via a pinned connection or pin 386 having a central axis 387 perpendicular to axis 322 in top view. Pin 386 is coupled to intermediate plate 390 via a linkage mechanism or link 388 having a first end 388a coupled to pin 386 and a second end 388b pivotably coupled to translatable plate 390. When paddle 382 is depressed, pin 386 is rotated in a counterclockwise direction as shown in FIG. 25, thereby causing link 388 to correspondingly rotate in a counterclockwise direction. The counterclockwise rotation of link 388 in turn causes intermediate plate 390 to be displaced upwards as shown in FIG. 25 along axis 395 due to the pivotable coupling between plate 390 and the second end 388b of link 388. As outer plate 390 moves axially upward relative to dial 398, teeth 392b are also displaced upward, thereby disengaging teeth 392b from teeth 398b of dial 398 and allowing relative rotation between plate 390 of boot 350 and dial 380 about axis 322. Further, as intermediate plate 390 is displaced upwards along central axis 395, biasing members 396 are compressed within elongate apertures 394. Thus, upon release of force on paddle 382, biasing members 396 bias intermediate plate 395 axially downwards (relative to axis 395) to the locked position with teeth 398b positively engaging teeth 392b.

Referring to FIGS. 1, 9-12, 23, and 24, drape hanger assembly 222 is coupled to the upper end 204*a* of housing 204 and is configured to support and position a drape during a medical procedure using system 10. In this embodiment, drape hanger assembly 222 includes a block or holder 224 secured to housing 204, a pair of horizontal drape hangers 228*a* releasably secured to holder 224 with locks 226, and a pair of vertical drape hangers 228*b* releasably secured to holder 224 with locks 226. One end of each hanger 228*a*, 228*b* is seated in a mating counterbore in holder 224 and secured therein with one lock 226 and the other end of each hanger 228*a*, 228*b* distal holder 224 includes a loop 228*c* for the securing a sterilized drape thereto. In this embodiment, each lock 226 is a set screw. Although system 10 is shown and described as including both horizontal and vertical hangers 228*a*, 228*b*, respectively, in other embodiments, only incorporate horizontal hangers (e.g., hangers 228*a*) or vertical hangers (e.g., vertical hangers 228*b*), or no hangers at all. Further, although hanger assembly 222 is coupled to housing 204 in this embodiment, in other embodiments, the hanger assembly (e.g., hanger assembly 222) is coupled to the shaft of the base (e.g., shaft 208 of base 202) such that the hanger assembly rotates with the shaft about the central axis of the shaft (e.g., axis 205).

As is known in the art, sterile drapes are used to cover and isolate (i.e., prevent contact with) unsterilized equipment from the patient, surgeon, and medical personnel during a procedure. In general, components positioned below the drape do not necessarily need to be sterilized (since they are isolated), while those components positioned on the side of the drape proximal the patient's appendage to be operated upon and exposed must be sterilized to reduce the potential for infections. Embodiments described herein can be arranged so that the sterile drape can be positioned over any one or more components of system 10. For example, the entirety of the system 10, including support assembly 100, rail assembly 200, and foot holder assembly 300 can be exposed, thereby necessitating sterilization of the entire system 10. Alternatively, a sterile drape can be positioned to isolate any one or more select components of system 10 such that those components need not be sterilized, while any exposed components must be sterilized.

Figure 28:
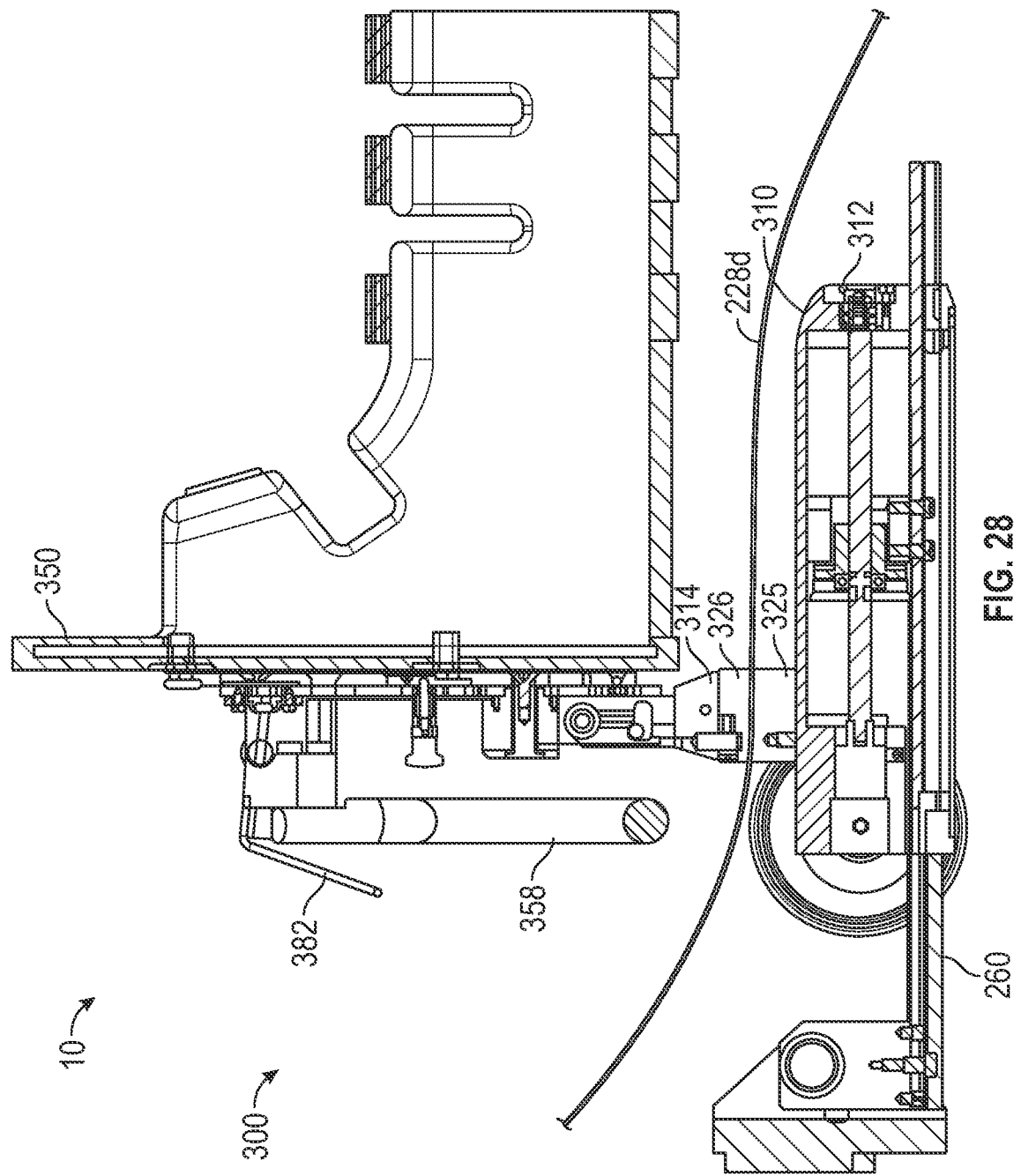
FIG. 28 is a cross-sectional view of the foot holder assembly of FIG. 18 taken along section 22-22 of FIG. 21 illustrating a sterile drape configuration in accordance with the principles disclosed herein.

In an exemplary preferred configuration shown in FIGS. 28-30, a sterile drape 228*d* is positioned below sterilized boot 350 and above horizontal rail 260. In particular, the drape 228*d* is disposed between blocks 325, 326. It should be appreciated that drape 228*d* can be positioned between blocks 325, 326 before sliding block 326 over block 325 via the dovetail connection, in which case drape 228*d* is squeezed or pinched between blocks 325, 326. In such a configuration, only the components of system 10, and more specifically the components of foot holder assembly 300, disposed "above" fixed block 325 and drape 228*d* need to be sterilized, while the remaining components of system 10 disposed below fixed block 325 and drape 228*d* need not be sterilized. Even with drape 228*d* pinched between blocks 325, 326, boot 350 can be easily and conveniently removed via quick release mechanism 327 without disturbing sterile drape 228*d* or contacting any unsterilized components therebelow. In this manner, boot 350 may be removed from system 10 or swapped for another boot while retaining the position and integrity of sterile drape 228*d*.

Figure 29:
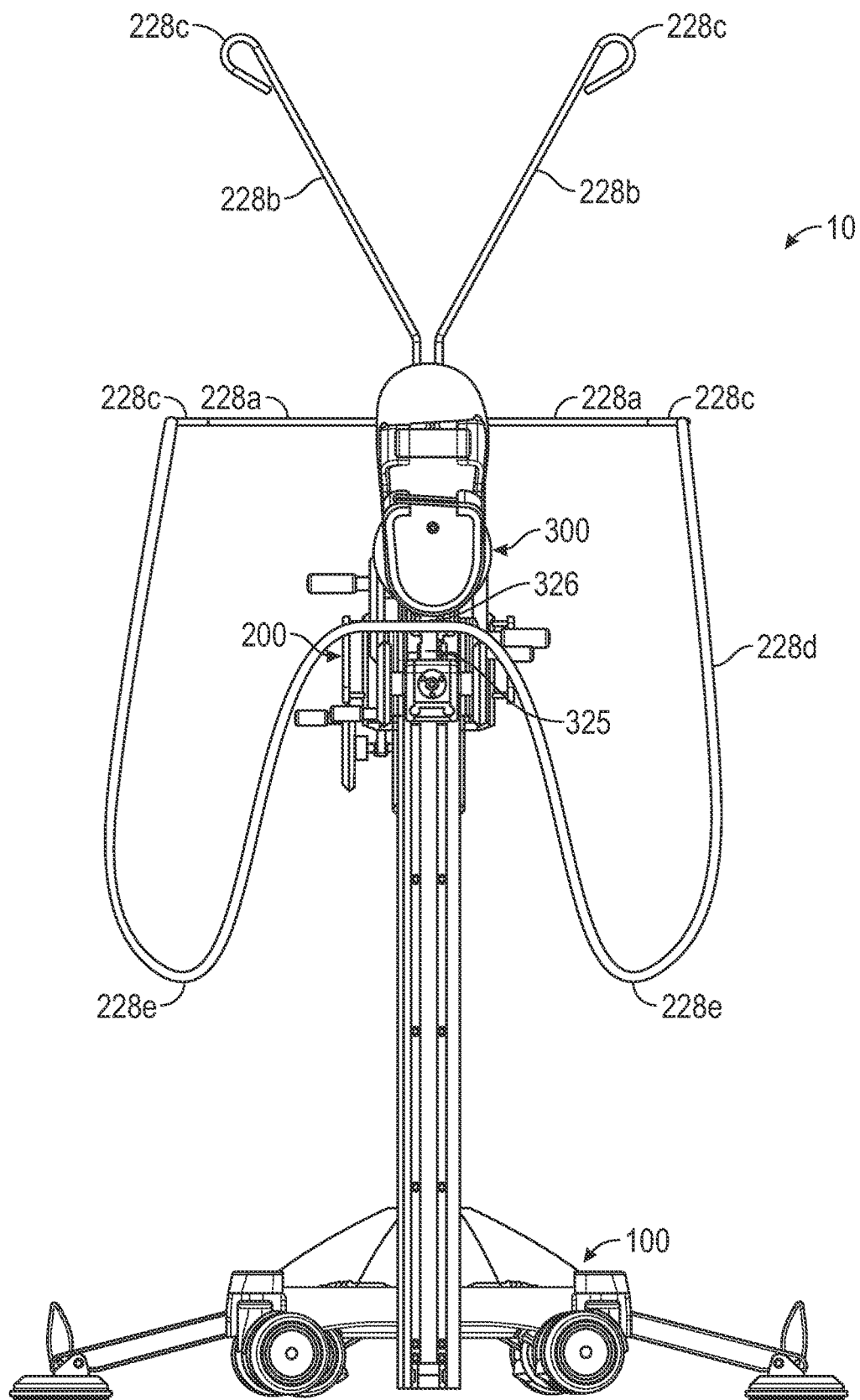
FIG. 29 is a front view of the leg support and manipulation system of FIG. 1 in a first or upper position, illustrating the sterile drape configuration of FIG. 28.
Figure 30:
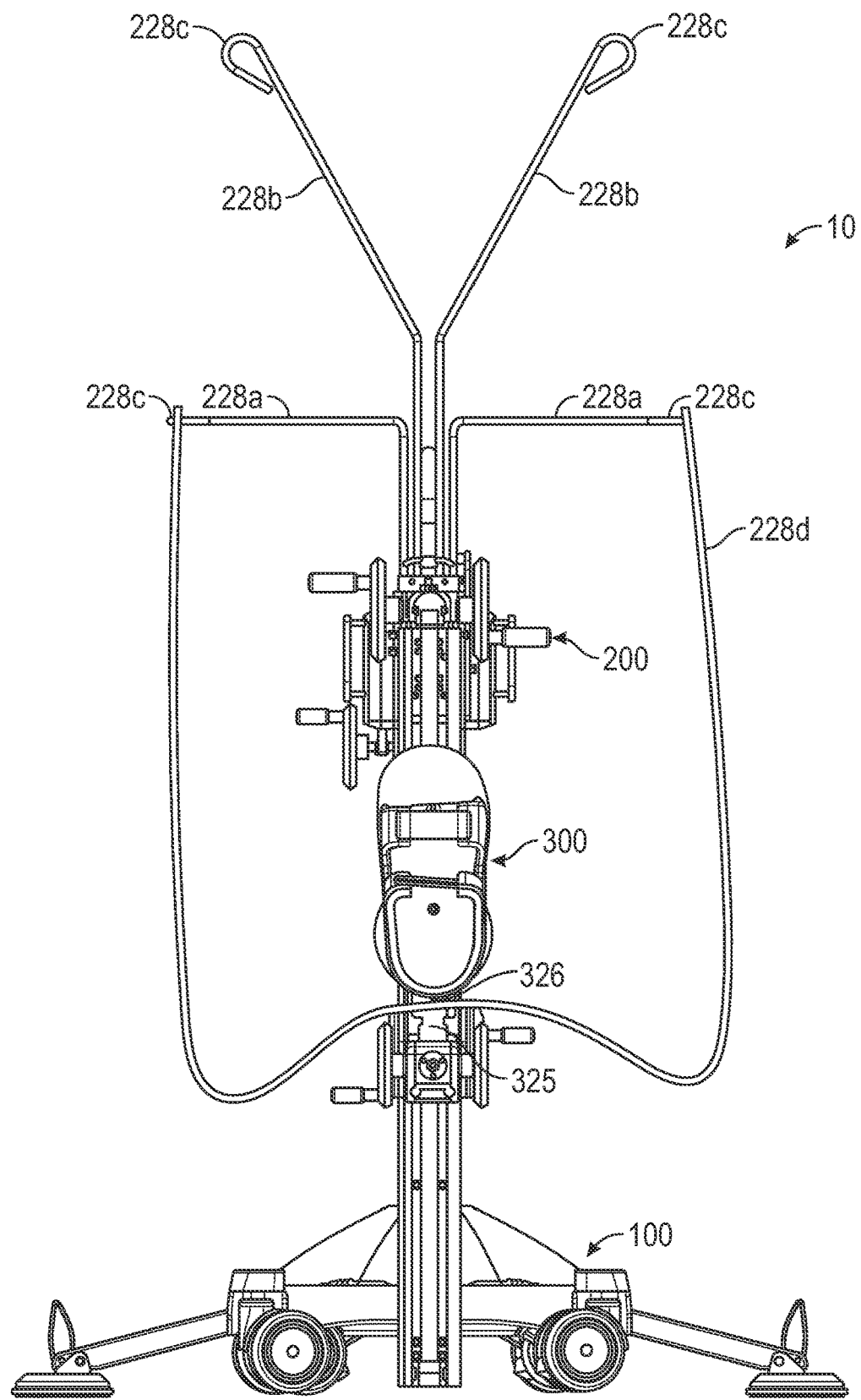
FIG. 30 is a front view of the leg support and manipulation system of FIG. 1, in a second or lower position illustrating the sterile drape configuration of FIG. 28.

As shown in FIGS. 29 and 30, the positioning of horizontal drape hangers 228*a* enable foot holder assembly 300 to be moved up and down along rail 250 without allowing sterile drape 228*d* to contact the ground, which would undesirable compromise the sterility of drape 228*d*. More specifically, horizontal hangers 228*a* are disposed above rail 260 and positioned on opposite sides of rail 260 in top view. This allows drape 228*d* to be positioned between blocks 325, 326 and secured to both hangers 228*a*. Drape 228*d* is preferably sized and positioned relative to hangers 228*a* and blocks 325, 326 such that there is slack 228*e* in drape 228*d* between blocks 325, 326 and each hanger 228*a* with foot holder assembly 300 and rail 260 in an upper position (e.g., uppermost position) proximal upper end 250*a* of vertical rail 250 shown in FIG. 29. The slack 228*e* in drape 228*d* is preferably sufficient such that foot holder assembly 300 can be displaced downward to a lower position (e.g., lowermost position) distal upper end 250*a* of vertical rail 250 as shown in FIG. 30 without placing drape 228*d* in tension between blocks 325, 326 and either hanger 322 or pulling drape 228*d* from either hangers 228*a*. Further, by clamping opposite ends or lateral sides of sterile drape 228*d* to horizontal rails 228*a*, which are positioned distal the ground, drape 228*d* is prevented from touching the ground for any position of foot holder assembly 300 along vertical rail 250.

Referring now to FIGS. 1-4, during an analytical or surgical procedure, the leg support and manipulation system 10 disclosed herein is positioned adjacent a patient's bed or operating table, and the patient's foot is secured in boot 350. The patient's foot can then be positioned and manipulated using system 10 to achieve the desired positioning and manipulation of the corresponding affected leg. Leg support and manipulation system 10 provides a plurality of degrees of freedom for positioning and manipulating the patient's foot, and hence corresponding leg. For example, post assembly 160 can be extended or contracted telescopically, shaft 208 can be rotated in either direction to rotate carrier 230 (and hence guide rails 250, 260) about axis 207, carrier 230 (and hence guide rails 250, 260) can be pivoted in either direction about axis 205, mounting block 262 (and hence horizontal guide rail 260) can be moved in either direction along vertical guide rail 250, carriage 310 (and hence boot 350) can be moved in either direction along horizontal guide rail 260, and boot 350 can be rotated in either direction about axes 322 and 326. Each of these movements can be selectively and independently controlled and adjusted. It should also be appreciated that leg support and manipulation system 10 itself can be moved along the ground to provide yet additional degrees of freedom of movement.

In an exemplary procedure, system 10 is positioned adjacent the end of the bed supporting the patient's hips. Wheels 126 permit the multi-directional rolling and positioning of the system 10 as desired. Once the desired position of system 10 relative to the patient is achieved, stabilizers 140 are deployed, pads 144 are secured to the ground, and wheels 126 are locked with locks 128. Next, the foot of the patient's operative leg is secured in boot 350. The boot 350 is fastened around the foot and ankle of the operative leg such that the operative leg is at least partially supported by the system 10 and can be positioned and manipulated with system 10. If necessary before or during the procedure, pads 144 can be released from the ground, stabilizers slightly raised about pivot points 142, and wheels 114 unlocked to adjust and reposition system 10. However, prior to subsequent positioning and manipulation of the patient's operative leg, stabilizers 140 are preferably deployed with pads 144 secured to the ground and wheels 126 are preferably locked via locks 128.

With leg support and manipulation system 10 secured at the desired position along the ground, boot 350 is positioned and manipulated via extension or contraction of post assembly 160, rotation of shaft 208 about axis 205 in either direction, rotation of boot 350 about axes 322 and 326 in either direction, pivoting of carrier 230 in either direction about axis 213, movement of mounting block 262 in either direction along vertical guide rail 250, movement of carriage 310 in either direction along horizontal guide rail 260, or combinations thereof. It should be appreciated that certain motions and combinations of motions result in the application of traction to the patient's operative leg.

In general, the components of leg support and manipulation system 10 can be constructed of any suitable material(s), but are preferably constructed of material(s) that can be sterilized, for example by an autoclave. Suitable materials include, without limitation, composites, plastics, metals and metal alloys, or combinations thereof. As previously described, leg support and manipulation system 10 is modular, thereby enabling the replacement of worn or damaged parts without having to replace the entirety of system 10. Such modularity also enables the components of system 10 to be selectively and independently sterilized. This may be particular beneficial in cases where select components are exposed during the procedure (i.e., not covered by sterile drapes), and thus, must be sterilized, while other components are not exposed during the procedure (i.e., covered by sterile drapes), and thus, need not be sterilized.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

The invention claimed is:

1. A freestanding system for applying traction to a patient independent of a table or bed, the system comprising:
 a base and a stabilizer arm moveably coupled to the base, wherein the stabilizer arm has a first end pivotally coupled to the base and a second end distal the base, and wherein the stabilizer arm is configured to pivot relative to the base about the corresponding first end; and
 a pad coupled to the second end of the stabilizer arm, wherein the pad comprises a suction device configured to releasably secure the second end of the corresponding stabilizer arm to ground, wherein the pad is configured to maintain the position of the system in response to the application of traction to the patient.

2. The system of claim 1, wherein the pad has a locked position with the pad fixably secured to ground and an unlocked position with the pad released from ground.

3. The system of claim 2, further comprising an actuator configured to transition the pad between the locked positions and the unlocked positions.

4. The system of claim 3, wherein the actuator comprises an air pump configured to selectably generate and relieve a pressure differential between within the suction device and air in a surrounding ambient environment.

5. The system of claim 3, wherein the air pump is electronically controlled.

6. The System of claim 1, further comprising:
 a vertically extendable post having a first end coupled to the base and a second end distal the base;
 a carrier pivotally coupled to the second end of the post, wherein the carrier is configured to pivot about a horizontal axis relative to the post;
 a first guide rail coupled to the carrier and configured to pivot with the carrier relative to the post, wherein the first guide rail has a longitudinal axis;
 a second guide rail pivotally coupled to the first guide rail, wherein the second guide rail is configured to move axially along the first guide rail; and
 a boot moveably coupled to the second guide rail, wherein the boot is configured to receive and retain at least a portion of a foot of the patient.

7. The system of claim 6, wherein the boot is pivotably coupled to the second guide rail and is configured to pivot relative to the second guide rail about a pivot axis disposed in a vertical plane oriented perpendicular to a longitudinal axis of the second guide rail.

8. The system of claim 7, wherein:
 the boot is rotatably coupled to the second guide rail and configured to rotate about a rotational axis oriented perpendicular to a rigid sole of the boot; and
 the system further comprises a release mechanism coupled to the boot, wherein the release mechanism has a locked position preventing rotation of the boot about the rotational axis and an unlocked position allowing rotation of the boot about the rotational axis.

9. The system of claim 6, wherein the boot is movably coupled to the first guide rail with a carriage, and wherein the carriage is configured to be controllably moved axially relative the first guide rail; and
 wherein the carriage is configured to move axially relative the first guide rail in a first axial direction and a second axial direction by rotating a spindle gear disposed in the carriage, and wherein the carriage is configured to move axially relative to the first guide rail in the second axial direction in response to the application of a force in the second axial direction to the carriage.

10. The system of claim 1, further comprising a boot moveably coupled to the base, wherein the boot is configured to receive and retain at least a portion of a foot of the patient, wherein the pad is configured to resist loads applied to the boot.

11. The system of claim 1, wherein the pad comprises an outer housing coupled to the second end of the corresponding stabilizer arm, a suction cup disposed within the housing, an actuator pivotally coupled to second end of the corresponding stabilizer arm, and a coupling link extending between the actuator and the suction cup, wherein the actuator is configured to transition the corresponding pad between the locked position and the unlocked position.

12. A freestanding system for applying traction to a patient independent of a table or bed, the system comprising:
 a base positionable on ground and a stabilizer arm pivotally coupled to the base, wherein the stabilizer arm has a first end pivotally coupled to the base and a second end distal the base, and wherein the stabilizer arms are configured to pivot relative to the base about the first ends; and
 a pad coupled to the second end of the stabilizer arm, wherein the pad comprises an actuator configured to selectively apply a low pressure region between the pad and ground to releasably secure the second end of the corresponding stabilizer arm to ground.

13. The system of claim 12, further comprising:
a vertically extendable post having a first end coupled to the base and a second end distal the base;
a carrier pivotally coupled to the second end of the post, wherein the carrier is configured to pivot about a horizontal axis relative to the post;
a first guide rail coupled to the carrier and configured to pivot with the carrier relative to the post, wherein the first guide rail has a longitudinal axis;
a second guide rail pivotally coupled to the first guide rail, wherein the second guide rail is configured to move axially along the first guide rail; and
a boot moveably coupled to the second guide rail, wherein the boot is configured to receive and retain at least a portion of a foot of the patient.

14. The system of claim 13, wherein the boot is pivotably coupled to the second guide rail and is configured to pivot relative to the second guide rail about a pivot axis disposed in a vertical plane oriented perpendicular to a longitudinal axis of the second guide rail;
wherein the boot is rotatably coupled to the second guide rail and configured to rotate about a rotational axis oriented perpendicular to a rigid sole of the boot.

15. The system of claim 14, further comprising a release mechanism coupled to the boot, wherein the release mechanism has a locked position preventing rotation of the boot about the rotational axis and an unlocked position allowing rotation of the boot about the rotational axis.

16. The system of claim 12, wherein the actuator comprises an air pump.

17. The system of claim 16, wherein the air pump is electronically controlled.

18. The system of claim 12, wherein the pad comprises an outer housing coupled to the second end of the corresponding stabilizer arm, a suction cup disposed within the housing, a coupling link extending between the actuator and the suction cup, and wherein the actuator is coupled to the second end of the corresponding stabilizer.

19. The system of claim 12, wherein the actuator comprises a handle actuatable between an unlocked position and a locked position configured to form the vacuum between the pad and ground.

20. The system of claim 12, wherein the pad comprises a suction device configured to resist loads applied to the system.

* * * * *